(12) United States Patent
Green et al.

(10) Patent No.: US 7,025,648 B2
(45) Date of Patent: Apr. 11, 2006

(54) LIQUID MANUFACTURING PROCESSES FOR PANEL LAYER FABRICATION

(75) Inventors: Albert M. Green, Springfield, VA (US); E. Victor George, Temecula, CA (US); N. Convers Wyeth, Oakton, VA (US)

(73) Assignee: Science Applications International Corporation, San Diego, CA (US)

( * ) Notice: Subject to any disclaimer, the term of this patent is extended or adjusted under 35 U.S.C. 154(b) by 185 days.

(21) Appl. No.: 10/789,976

(22) Filed: Mar. 2, 2004

(65) Prior Publication Data

US 2004/0166762 A1    Aug. 26, 2004

Related U.S. Application Data

(63) Continuation of application No. 10/214,740, filed on Aug. 9, 2002, now Pat. No. 6,764,367, which is a continuation-in-part of application No. 09/697,344, filed on Oct. 27, 2000, now Pat. No. 6,612,889.

(51) Int. Cl.
  *H01J 9/24*    (2006.01)
(52) U.S. Cl. .......................................... 445/24; 445/58
(58) Field of Classification Search .................. 445/24, 445/58
  See application file for complete search history.

(56) References Cited

U.S. PATENT DOCUMENTS

| | | | |
|---|---|---|---|
| 3,559,190 A | 1/1971 | Blitzer et al. | ................ 340/173 |
| 3,646,384 A | 2/1972 | Lay | ........................... 313/109.5 |
| 3,704,052 A | 11/1972 | Coleman | ..................... 316/17 |
| 3,704,386 A | 11/1972 | Cola | ........................ 313/108 R |
| 3,755,027 A | 8/1973 | Gilsing | ......................... 156/67 |
| 3,848,248 A | 11/1974 | MacIntyre, Jr. | ........ 340/324 M |
| 3,969,651 A | 7/1976 | Greeson, Jr. | ........... 315/169 TV |
| 3,990,068 A | 11/1976 | Mayer et al. | ........... 340/324 M |
| 3,998,618 A | 12/1976 | Kreick et al. | .................. 65/105 |
| 4,027,246 A | 5/1977 | Caccoma et al. | ........ 235/151.1 |
| 4,035,690 A | 7/1977 | Roeber | ................. 315/169 TV |

(Continued)

FOREIGN PATENT DOCUMENTS

JP    4-287397    10/1992

(Continued)

OTHER PUBLICATIONS

Preliminary Examination Report for Application No. PCT/US01/42805, dated Dec. 21, 2004 (mailing date).

(Continued)

*Primary Examiner*—Joseph Williams
(74) *Attorney, Agent, or Firm*—Kilpatrick Stockton LLP

(57) ABSTRACT

A method for manufacturing a light-emitting panel sandwiches a plurality of micro-components between two flexible substrates in a web configuration. Each micro-component contains a gas or gas-mixture capable of ionization when a sufficiently large voltage is supplied across the micro-component via at least two electrodes. The micro-components are disposed in sockets formed at pre-determined locations in a first dielectric substrate so that they are adjacent to electrodes imprinted in the first substrate. Dielectric layers and the conductors for acting as electrodes are formed using liquid processes or combined liquid and sheet processes, where liquid materials are applied to the surface of the underlying layer, then cured to complete the formation of layers. The assembled layers are coated with a protective coating and may include an RF shield. In one embodiment, patterning of the conductors is achieved by applying conductive ink using an ink jet process. In another embodiment, the conductors may be patterned photolithographically using a leaky optical waveguide as a contact mask.

39 Claims, 15 Drawing Sheets

U.S. PATENT DOCUMENTS

| | | | |
|---|---|---|---|
| 4,303,433 A | 12/1981 | Torobin | 65/21.4 |
| 4,379,301 A | 4/1983 | Fischbeck | 346/1.1 |
| 4,386,358 A | 5/1983 | Fischbeck | 346/1.1 |
| 4,393,326 A | 7/1983 | Kamegaya et al. | 313/582 |
| 4,429,303 A | 1/1984 | Aboelfotoh | 340/701 |
| 4,534,743 A | 8/1985 | D'Onofrio et al. | 445/24 |
| 4,554,537 A | 11/1985 | Dick | 340/775 |
| 4,563,617 A | 1/1986 | Davidson | 315/312 |
| 4,591,847 A | 5/1986 | Criscimagna et al. | 340/776 |
| 4,654,561 A | 3/1987 | Shelton | 315/111.71 |
| 4,658,269 A | 4/1987 | Rezanka | 346/75 |
| 4,697,123 A | 9/1987 | Shinoda et al. | 315/169.4 |
| 4,728,864 A | 3/1988 | Dick | 315/169.3 |
| 4,833,463 A | 5/1989 | Dick et al. | 340/775 |
| 4,843,281 A | 6/1989 | Mendelsohn | 313/587 |
| 4,887,003 A | 12/1989 | Parker | 313/634 |
| 4,912,364 A | 3/1990 | Holló et al. | 313/623 |
| 5,019,807 A | 5/1991 | Stapleton et al. | 340/718 |
| 5,030,888 A | 7/1991 | Salavin et al. | 315/169.4 |
| 5,062,916 A | 11/1991 | Aufderheide et al. | 156/269 |
| 5,068,916 A | 11/1991 | Harrison et al. | 455/39 |
| 5,075,597 A | 12/1991 | Salavin et al. | 315/169.4 |
| 5,126,632 A | 6/1992 | Parker | 313/634 |
| 5,150,007 A | 9/1992 | Andreadakis | 313/586 |
| 5,315,129 A | 5/1994 | Forrest et al. | 257/21 |
| 5,396,149 A | 3/1995 | Kwon | 313/486 |
| 5,500,287 A | 3/1996 | Henderson | 428/403 |
| 5,501,871 A | 3/1996 | Henderson | 427/160 |
| 5,510,678 A | 4/1996 | Sakai et al. | 315/58 |
| 5,514,934 A | 5/1996 | Matsumoto et al. | 313/607 |
| 5,674,351 A | 10/1997 | Lovoi | 156/629.1 |
| 5,675,212 A | 10/1997 | Schmid et al. | 313/422 |
| 5,686,790 A | 11/1997 | Curtin et al. | 313/493 |
| 5,703,436 A | 12/1997 | Forrest et al. | 313/506 |
| 5,707,745 A | 1/1998 | Forrest et al. | 428/432 |
| 5,721,160 A | 2/1998 | Forrest et al. | 438/28 |
| 5,725,787 A | 3/1998 | Curtin et al. | 216/25 |
| 5,746,635 A | 5/1998 | Spindt et al. | 445/24 |
| 5,747,931 A | 5/1998 | Riddle et al. | 313/581 |
| 5,755,944 A | 5/1998 | Haven et al. | 204/486 |
| 5,757,026 A | 5/1998 | Forrest et al. | 257/40 |
| 5,757,131 A | 5/1998 | Tsuchiya | 375/582 |
| 5,757,139 A | 5/1998 | Forrest et al. | 315/169.3 |
| 5,777,782 A | 7/1998 | Sheridon | 359/296 |
| 5,788,814 A | 8/1998 | Sun et al. | 204/297 R |
| 5,793,158 A | 8/1998 | Wedding, Sr. | 313/493 |
| 5,798,604 A | 8/1998 | Duboc, Jr. et al. | 313/495 |
| 5,808,403 A | 9/1998 | Clerc | 313/336 |
| 5,811,833 A | 9/1998 | Thompson | 257/40 |
| 5,815,306 A | 9/1998 | Sheridon et al. | 359/296 |
| 5,825,451 A | 10/1998 | Ma et al. | 349/187 |
| 5,837,221 A | 11/1998 | Bernstein et al. | 424/9.52 |
| 5,844,363 A | 12/1998 | Gu et al. | 313/506 |
| 5,853,446 A | 12/1998 | Carre et al. | 65/17.3 |
| 5,862,054 A | 1/1999 | Li | 364/468.28 |
| 5,865,657 A | 2/1999 | Haven et al. | 445/24 |
| 5,897,414 A | 4/1999 | Bergeron et al. | 445/3 |
| 5,898,266 A | 4/1999 | Spindt et al. | 313/495 |
| 5,913,704 A | 6/1999 | Spindt et al. | 445/24 |
| 5,914,150 A | 6/1999 | Porter et al. | 427/77 |
| 5,917,646 A | 6/1999 | Sheridon | 359/296 |
| 5,920,080 A | 7/1999 | Jones | 257/40 |
| 5,939,826 A | 8/1999 | Ohsawa et al. | 313/586 |
| 5,945,174 A | 8/1999 | Shaw et al. | 427/509 |
| 5,949,513 A | 9/1999 | Ma et al. | 349/187 |
| 5,953,587 A | 9/1999 | Forrest et al. | 438/99 |
| 5,964,630 A | 10/1999 | Slusarczuk et al. | 445/25 |
| 5,965,109 A | 10/1999 | Lohrmann | 424/9.52 |
| 5,967,871 A | 10/1999 | Kaake et al. | 445/24 |
| 5,969,472 A | 10/1999 | Kisner | 313/484 |
| 5,975,683 A | 11/1999 | Smith et al. | 347/55 |
| 5,984,747 A | 11/1999 | Bhagavatula et al. | 445/24 |
| 5,985,460 A | 11/1999 | Wang et al. | 428/426 |
| 5,986,409 A | 11/1999 | Farnworth et al. | 315/169.4 |
| 5,990,614 A | 11/1999 | Spindt | 313/495 |
| 5,990,620 A | 11/1999 | Lepselter | 313/585 |
| 6,002,198 A | 12/1999 | Spindt et al. | 313/292 |
| 6,013,538 A | 1/2000 | Burrows et al. | 438/22 |
| 6,017,584 A | 1/2000 | Albert et al. | 427/213.3 |
| 6,019,657 A | 2/2000 | Chakvorty et al. | 445/24 |
| 6,022,652 A | 2/2000 | Haven et al. | 430/26 |
| 6,023,259 A | 2/2000 | Howard et al. | 345/76 |
| 6,025,097 A | 2/2000 | Drumm | 430/7 |
| 6,030,269 A | 2/2000 | Drumm | 445/52 |
| 6,030,715 A | 2/2000 | Thompson et al. | 428/690 |
| 6,033,547 A | 3/2000 | Trau et al. | 204/622 |
| 6,037,710 A | 3/2000 | Poole et al. | 313/422 |
| 6,037,918 A | 3/2000 | Hansen et al. | 345/74 |
| 6,038,002 A | 3/2000 | Song | 349/43 |
| 6,039,619 A | 3/2000 | Kang et al. | 445/24 |
| 6,045,930 A | 4/2000 | Thompson et al. | 428/690 |
| 6,046,543 A | 4/2000 | Bulovic et al. | 313/504 |
| 6,048,469 A | 4/2000 | Xiang et al. | 252/301.6 R |
| 6,048,630 A | 4/2000 | Burrows et al. | 428/690 |
| 6,049,366 A | 4/2000 | Hakemi et al. | 349/86 |
| 6,069,443 A | 5/2000 | Jones et al. | 313/504 |
| 6,072,276 A | 6/2000 | Okajima | 313/581 |
| 6,079,814 A | 6/2000 | Lean et al. | 347/55 |
| 6,080,606 A | 6/2000 | Gleskova et al. | 438/151 |
| 6,087,196 A | 7/2000 | Sturm et al. | 438/29 |
| 6,091,195 A | 7/2000 | Forrest et al. | 313/504 |
| 6,091,380 A | 7/2000 | Hashimoto et al. | 345/60 |
| 6,091,874 A | 7/2000 | Higashi et al. | 384/130 |
| 6,097,147 A | 8/2000 | Baldo et al. | 313/506 |
| 6,130,655 A | 10/2000 | Lammers | 345/72 |
| 6,137,553 A | 10/2000 | Izumi et al. | 349/49 |
| 6,201,518 B1 | 3/2001 | Kane et al. | 345/60 |
| 6,255,777 B1 | 7/2001 | Kim et al. | 313/582 |
| 6,262,706 B1 | 7/2001 | Albert et al. | 345/107 |
| 6,265,826 B1 | 7/2001 | Miyazaki | 313/586 |
| 6,281,863 B1 | 8/2001 | Sasaki et al. | 345/60 |
| 6,285,129 B1 | 9/2001 | Park et al. | 313/586 |
| 6,285,434 B1 | 9/2001 | Ma et al. | 349/189 |
| 6,288,488 B1 | 9/2001 | Amemiya | 313/582 |
| 6,288,693 B1 | 9/2001 | Song et al. | 345/68 |
| 6,291,925 B1 | 9/2001 | Jacobson | 310/319 |
| 6,292,159 B1 | 9/2001 | Someya et al. | 345/60 |
| 6,292,160 B1 | 9/2001 | Mikoshiba et al. | 345/60 |
| 6,295,040 B1 | 9/2001 | Nhan et al. | 345/60 |
| 6,296,539 B1 | 10/2001 | Awaji et al. | 445/24 |
| 6,297,590 B1 | 10/2001 | Nanto et al. | 313/586 |
| 6,300,152 B1 | 10/2001 | Kim | 438/30 |
| 6,300,932 B1 | 10/2001 | Albert | 345/107 |
| 6,304,031 B1 | 10/2001 | Wani et al. | 313/582 |
| 6,304,032 B1 | 10/2001 | Asano | 313/582 |
| 6,304,238 B1 | 10/2001 | Tsuchida | 345/87 |
| 6,307,319 B1 | 10/2001 | Lee | 313/590 |
| 6,312,304 B1 | 11/2001 | Duthaler et al. | 445/24 |
| 6,312,971 B1 | 11/2001 | Amundson et al. | 438/99 |
| 6,319,325 B1 | 11/2001 | Hiratsuka et al. | 118/718 |
| 6,322,010 B1 | 11/2001 | Sasaki et al. | 239/568 |
| 6,545,422 B1 | 4/2003 | George et al. | 315/169.3 |
| 6,570,335 B1 | 5/2003 | George et al. | 315/169.3 |
| 6,612,889 B1 | 9/2003 | Green et al. | 445/24 |
| 2001/0008825 A1 | 7/2001 | Toyoda et al. | 445/24 |
| 2001/0033256 A1 | 10/2001 | Moore | 345/60 |
| 2001/0053570 A1 | 12/2001 | Kido | 438/149 |
| 2002/0008470 A1 | 1/2002 | Uegaki et al. | 313/567 |
| 2002/0009536 A1 | 1/2002 | Iguchi et al. | 427/10 |
| 2002/0016075 A1 | 2/2002 | Peng et al. | 438/700 |
| 2002/0017864 A1 | 2/2002 | Watanabe et al. | 313/586 |
| 2002/0022565 A1 | 2/2002 | Sreeram et al. | 501/16 |
| 2002/0024295 A1 | 2/2002 | Miyashita et al. | 313/495 |
| 2003/0094891 A1 | 5/2003 | Green et al. | 313/495 |

| | | |
|---|---|---|
| 2003/0164684 A1 | 9/2003 | Green et al. ............... 313/582 |

FOREIGN PATENT DOCUMENTS

| | | |
|---|---|---|
| JP | 10-3869 | 1/1998 |
| WO | WO 00/36465 | 6/2000 |

OTHER PUBLICATIONS

Preliminary Examination Report for Application No. PCT/US03/22868, dated Sep. 27, 2004 (mailing date).
International Search Report for Application No. PCT/US03/22868, dated Jun. 1, 2004 (mailing date).
Preliminary Examination Report for Application No. PCT/US01/42803, dated Sep. 22, 2003 (mailing date).
Preliminary Examination Report for Application No. PCT/US01/42782, dated Jun. 4, 2003 (mailing date).
International Search Report for Application No. PCT/US01/42805, dated Apr. 3, 2003 (mailing date).
Written Opinion for Application No. PCT/US01/42782, dated Dec. 31, 2002 (mailing date).
International Search Report for Application No. PCT/US01/42803, dated Dec. 9, 2002 (mailing date).
International Search Report for Application No. PCT/US01/42807, dated Dec. 8, 2002 (mailing date).
International Search Report for Application No. PCT/US01/51439, dated Sep. 23, 2002 (mailing date).
Written Opinion for Application No. PCT/US01/42807, dated Sep. 17, 2002 (mailing date).
International Search Report for Application No. PCT/US01/42807, dated May 20, 2002 (mailing date).
International Search Report for Application No. PCT/US01/42782, dated Apr. 11, 2002 (mailing date).
Sheats, James, "Introduction to Organic Light-Emitting Diodes (OLEDs)" [online], [retrieved on May 9, 2002], 8 pp., Retrieved from the Internet: http://www.rolltronics.com/intro_oled.htm.
Sauvante, Michael, "Roll-to-Roll Manufacturing" [online], [retrieved on May 9, 2002], 4 pp., Retrieved from the Internet: http://www.rolltronics.com/roll2roll.htm.
Veronis, Georgios and Inan, Umran S., "Optimization of the Luminous Efficiency of Plasma Display Panels Using Numerical Modeling" [online], [retrieved on Mar. 13, 2002], 8 pp., Retrieved from the Internet: http://www-star.stanford.edu/~vlf/plasma_display/index.htm.
Smilgys, Russell, et al., "Progress Toward Roll Processing of Solar Reflective Material," *Proceedings of Solar Forum 2001 Solar Engergy: The Power to Choose*, Washington, DC, 8 pp., Apr. 21-25, 2001.
Srinivasan, Uthara, et al., "Microstructure to Substrate Self-Assembly Using Capillary Forces," *Nournal of Microelectromechanical Systems*, vol. 10, No. 1, Mar., 2001, pp. 17-17-24.
Chutinan, Alongkarn and Noda, Susumu, "Waveguides and Waveguide Bends in Two-Dimensional Photonic Crystal Slabs," *The American Physical Society*, vol. 62, No. 7, 5 pp., Aug. 15, 2000.
"Rolltronics" [online], Feb. 20, 2000 [retrieved on Mar. 12, 2000], 13 pp., Retrieved from the Internet: http://www.rolltronics.com.
"Electronics & Telecommunications" [online], LG Electronics, Copyright 2001 [retrieved on Nov. 7, 2001], 1 p., Retrieved from the Internet: http://www.lg.co.kr/English/company/electronic/index.jsp?code=A3.
"New Product" [online], LG Electronics, Copyright 2001 [retrieved on Nov. 7, 2001], 1 p., Retrieved from the Internet: http://www.lge.com.

"Monitor" [online], LG Electronics, Copyright 2001 [retrieved on Nov. 7, 2001], 2 pp., Retrieved from the Internet: http://www.lgeus.com/Product/Monitor/newmonitors.asp.
"LG Electronics Introduces 42-Inch Digital PDP TV" [online], LG Electronics, Copyright 2001 [retrieved on Nov. 7, 2001], 2 pp., Retrieved from the Internet: http://www.pdpdisplay.com/eng/news/e_read.as?nSeqno=22.
"LG PDP Now Available at World Renowned Harrods Department Store" [online], LG Electronics, Copyright 2001 [retrieved on Nov. 7, 2001], 2 pp., Retrieved from the Internet: http://www.pdpdisplay.com/eng/news/e_read.asp?nSeqno21.
"LG Electronics Becomes First in Korea to Export PDP Module" [online], LG Electronics, Copyright 2001 [retrieved on Nov. 7, 2001], 2 pp., Retrieved from the Internet: http://www.pdpdisplay.com/eng/news/e_read.asp?nSeqNo=19&type=&word=.
"LG Electronics—To the Top in PDP Business" [online], LG Electronics, Copyright 2001 [retrieved on Nov. 7, 2001], 2 pp., Retrieved from the Internet: http://www.pdpdisplay.com/eng/news/e_read.asp?nSeqNo=16&type=&word=.
"LG Electronics Becomes the First in Korea to Export PDP" [online], LG Electronics, Copyright 2001 [retrieved on Nov. 7, 2001], 2 pp., Retrieved from the Internet: http://www.pdpdisplay.com/eng/news/e_read.asp?nSeqNo=14&type=&word=.
"LG Electronics Held the Ceremony for the completion of the PDP Factory" [online], LG Electronics, Copyright 2001 [retrieved on Nov. 7, 2001], 2 pp., Retrieved from the Internet: http://www.pdpdisplay.com/eng/news/e_read.asp?nSeqNo=13&type=&word.
"Runco PlasmaWall Systems with Vivex Processing" [online], Copyright 2001 [retrieved on Jan. 17, 2002], 2 pp., Retrieved from the Internet: http://www.runco.com/Products/Plasma/Default.htm.
"Runco PlasmaWall PL-42cx" [online], Copyright 2001 [retrieved on Jan. 17, 2002], 2 pp., Retrieved from the Internet: http://www.runco.com/Products/Plasma/PL42cx.htm.
"Runco PlasmaWall Pl-50c" [online], Copyright 2001 [retrieved on Jan. 17, 2002], 2 pp., Retrieved from the Internet: http://www.runco.com/Products/Plasma/PL50c.htm.
"Runco PlasmaWall™ PL-61cx" [online], Copyright 2001 [retrieved on Jan. 17, 2002], 2 pp., Retrieved from the Internet: http://www.runco.com/Products/Plasma/PL61.htm.
Alien Technology Corporation's Technology Overview; copyright © 2000, Alien Technology™; http://www.alientechnology.com/d/technology/overview.html.
Anonymous, *Alien Technology Corporation White Paper—Fluidic Self Assembly*, Alien Technology Corp., Oct. 1999, pp. 1-7.
Shin, Y. K., Lee, J. K., Shon, C. H., "Two-Dimensional Breakdown Characteristics of PDP Cells for Varying Geometry," *IEEE Transactions on Plasma Science*, vol. 27, No. 1, Feb., 1999, pp. 14-15.
Raulf, S., Kushner, M. J., "Operation of a Coplanar-Electrode Plasma Display Panel Cell," *IEEE Transactions on Plasma Science*, vol. 27, No. 1, Feb. 1999, pp. 10-11.

Kurihara, M., Makabe, T., "Two-Dimensional Modeling of a Micro-Cell Plasma in Xe Driven by High Frequency," *IEEE Transactions on Plasma Science*, vol. 27, No. 5, Oct., 1999, pp. 1372-1378.

Peterson, "Rethinking Ink" [online], Science News, vol. 153, No. 25, Jun. 20, 1998 [retrieved on Dec. 4, 2002], 7 pp., Retrieved from the Internet: http://www.sciencenews.org/sn_arc98/6_20_98/bob2.htm.

"Transparent Conductive Coatings," Copyright 1998, 4 pp.

Lin, Yi-Zhen, et al., "A New Method of Analyzing the Light Transmission in Leaky and Absorbing Planar Waveguides," *IEEE Photonics Technology Letters*, vol. 9, No. 9, Sep., 1997, pp. 1241-.

Jacobson, et al., "The Last Book" [online], IBM Systems Journal, vol. 36, No. 3, 1997 [retrieved on Dec. 4, 2002], 6 pp., Retrieved from the Internet: http://www.research.ibm.com/journal/sj/363/Jacobson.html.

Stearns, Thomas H., "Flexible Printed Circuitry," 6 pp., 1996.

"Flat Panel Displays in Perspective," 44 pp., Sep., 1995.

Franjione, et al., "The Art and Science of Microencapsulation" [online] Technology Today, Summer, 1995 [retrieved on Dec. 4, 2002], 10 pp., Retrieved from the Internet: http://www.swri.edu/3pubs/ttoday/summer95/microeng.htm.

LIQUID MANUFACTURING PROCESSES FOR PANEL LAYER FABRICATION

CROSS-REFERENCE TO RELATED APPLICATIONS

This application is a continuation of application Ser. No. 10/214,740, filed Aug. 9, 2002, now U.S. Pat. No. 6,764,367 entitled Liquid Manufacturing Processes for Panel Layer Fabrication, which is a continuation-in-part of application Ser. No. 09/697,344, filed Oct. 27, 2000, now U.S. Pat. No. 6,612,889, entitled Method for Making a Light-Emitting Panel, and is related to the following co-owned applications: Ser. No. 09/697,346, now U.S. Pat. No. 6,545,422, filed Oct. 27, 2000, entitled A Socket for Use with a Micro-Component in a Light-Emitting Panel; Ser. No. 09/697,358, filed Oct. 27, 2000, entitled: A Micro-Component for Use in a Light-Emitting Panel; Ser. No. 09/697,498, filed Oct. 27, 2000, now U.S. Pat. No. 6,620,012, entitled A Method for Testing a Light-Emitting Panel and the Components Therein; Ser. No. 09/697,345, filed Oct. 27, 2000, now U.S. Pat. No. 6,570,335, entitled A Method and System for Energizing a Micro-Component In a Light-Emitting Panel; Ser. No. 10/214,769, filed Aug. 9, 2002, entitled Use of Printing and Other Technology for Micro-Component Placement Ser. No. 10/214,716, filed Aug. 9, 2002, entitled Method of On-Line Testing of a Light-Emitting Panel Ser. No. 10/214,764, filed Aug. 9, 2002, entitled Method and Apparatus for Addressing Micro-Components in a Plasma Display Panel; and Ser. No. 10/214,768, filed Aug. 9, 2002, entitled Design, Fabrication, Conditioning, and Testing of Micro-Components for Use in a Light-Emitting Panel. Each of the above-identified applications is incorporated herein by reference in its entirety.

BACKGROUND OF THE INVENTION

1. Field of the Invention

The present invention is relates to a method for manufacturing a light-emitting panel and more particularly to a web fabrication process for manufacturing a light-emitting panel.

2. Description of Related Art

A number of different methods have been used or proposed for construction of plasma panel display devices in which a plasma-forming gas is enclosed between sets of electrodes which are used to excite the plasma. In one type of plasma display panel, wire electrodes are placed on the surfaces of parallel plates of glass so that they are spaced uniformly apart. The plates are then sealed together at the outer edges with the plasma forming gas filling the cavity formed between the parallel plates. Although widely used, this type of open display structure suffers from numerous disadvantages. The sealing of the outer edges of the parallel plates and the introduction of the plasma forming gas are both expensive and time-consuming processes, resulting in a costly end product. In addition, it is particularly difficult to achieve a good seal at the sites where the electrodes are fed through the ends of the parallel plates, which can result in gas leakage and a shortened product life. Another disadvantage is that individual pixels are not segregated within the parallel plates. As a result, gas ionization activity in a selected pixel during a write operation may spill over to adjacent pixels, thereby raising the undesirable prospect of possibly igniting adjacent pixels. Even if adjacent pixels are not ignited, the ionization activity can change the turn-on and turn-off characteristics of the nearby pixels.

In another type of known plasma display, individual pixels are mechanically isolated either by forming trenches in one of the parallel plates or by adding a perforated insulating layer sandwiched between the parallel plates. These mechanically isolated pixels, however, are not completely enclosed or isolated from one another because there is a need for the free passage of the plasma forming gas between the pixels to assure uniform gas pressure throughout the panel. While this type of display structure decreases spill over, spill over is still possible because the pixels are not in total electrical isolation from one another. In addition, in this type of display panel it is difficult to properly align the electrodes and the gas chambers, which may cause pixels to misfire. As with the open display structure, it is also difficult to get a good seal at the plate edges. Furthermore, it is expensive and time consuming to introduce the plasma producing gas and seal the outer edges of the parallel plates.

In yet another type of known plasma display, individual pixels are also mechanically isolated between parallel plates. In this type of display, the plasma forming gas is contained in transparent spheres formed of a closed transparent shell. Various methods have been used to contain the gas filled spheres between the parallel plates. In one method, spheres of varying sizes are tightly bunched and randomly distributed throughout a single layer, and sandwiched between the parallel plates. In a second method, spheres are embedded in a sheet of transparent dielectric material and that material is then sandwiched between the parallel plates. In a third method, a perforated sheet of electrically nonconductive material is sandwiched between the parallel plates with the gas filled spheres distributed in the perforations.

While each of the types of displays discussed above are based on different design concepts, the manufacturing approach used in their fabrication is generally the same: a batch fabrication process. It would be desirable to simplify and streamline the manufacturing process and to eliminate at least a portion of the steps which can have a negative impact on process yield and/or cost. The present invention is directed to such a method.

BRIEF SUMMARY OF THE INVENTION

According to the present invention, a novel flexible plasma display panel and methods for making such a panel involve a web fabrication process. In this display panel, the plasma forming gas is sealed in transparent micro-components formed of a closed transparent shell. The micro-components, which may be spheres, capillaries or virtually any other three-dimensional shape, are then coated with phosphors to emit one of the primary colors: red, green or blue. In the web fabrication process, a non-conductive flexible first substrate has electrodes imprinted thereon using known printing techniques, such as lithography or screen printing. In one variation, dimples are embossed in the first substrate to define locations at which micro-components are to be placed relative to the electrodes. In another variation, the micro-components are electrostatically drawn to the correct locations relative to the electrodes. After affixing the micro-components in place, and possibly testing to ensure complete and proper placement of the micro-components, a second substrate, also in web form, is disposed over the first substrate so that the micro-components are sandwiched between the first and second substrates. Additional electrodes may be patterned on the second substrate, and the second substrate may be applied as more than one layer to create one or more dielectric/electrode sandwiches near the micro-component to provide additional sustain electrodes or addressing electrodes. Alternatively, the second substrate can be preformed with embedded electrodes which are then aligned with the micro-components when the second substrate is applied. A protective layer may be placed on top of the second substrate, then the layered assembly is diced to form individual light-emitting panels of the desired size.

In a second embodiment of the present invention, a light-emitting panel is formed on a first substrate comprising a flexible web material. A conductive film is patterned on the first substrate to define a plurality of electrodes and dimples are formed to define locations in which gas-filled micro-components, which emit light when excited, are to be located. An adhesive material may be deposited into the dimples. The micro-components are then applied to fill the dimples, where they are held in place by the adhesive. Application of the micro-components to the first substrate can be achieved by a number of different methods including use of a drop tower or an ink-jet type dispenser, or by running the first substrate through a shaker bath filled with an excess of micro-components. An electrostatic charge may be applied to the first substrate to draw the micro-components to the desired locations. After the micro-components are affixed to the first substrate, a liquid dielectric material is applied to the surface of the first substrate using known methods such a vacuum or atmospheric coating, which may include chemical vapor deposition (CVD), plasma sputtering, electron-beam deposition, injection of coating fluid under pressure, screen printing or similar processes. The conditions under which the liquid dielectric are applied, e.g., the surface energy and surface tension of the liquid, are selected to ensure good wetting of the micro-components, i.e., so that the dielectric material is in contact with the surfaces of the micro-components without bubbles or gaps. Further, the liquid dielectric should be applied with a uniform thickness across the first substrate so that the spacing between the excitation electrodes is uniform across the display. Depending on the deposition process that was used, the liquid dielectric is then cured to remove any solvents and other volatile agents that were included in the liquid to facilitate fluid delivery, leaving the micro-components embedded in the flexible, cured dielectric layer. In a preferred embodiment, the liquid dielectric is coated so as to form a dielectric layer with a thickness corresponding to about half the height of the micro-component, allowing a mid-plane conductor to be formed near the micro-components.

Electrodes are formed by applying a conductive liquid to the upper surface of the dielectric layer. The electrodes may be patterned using known lithographic methods, e.g., conductive film deposition, photoresist deposition, masked exposure and development of the photoresist followed by etching to remove the unprotected film, or by printing, e.g., ink-jet printing with a conductive ink. In an alternative embodiment, conductive liquids that are selectively drawn to the desired locations using one or more characteristics of the liquid including surface tension, viscosity, thickness and electrical conductivity in combination with surface characteristics of the dielectric layer. For example, where channels or depressions in the dielectric layer may act as guides for distribution of a liquid conductor to the desired locations near the micro-components, so that no alignment is required in the step for forming the electrodes.

A second application of liquid dielectric material coats the upper surface of the previous dielectric layer, mid-plane conductor and the surfaces of the micro-components above the mid-plane point. An additional sequence of depositing a liquid dielectric and a patterned conductive film may be added before "topping off" the layers with a final coating of liquid dielectric to form a layer that approaches, but not does not cover, the tops of the micro-components. A protective cover layer is then placed over top of the entire assembly, then the panels are diced into the desired dimensions. The cover layer is preferably a web material that may be applied according to known web manufacturing methods.

In an alternate method for patterning of electrodes using photolithographic methods, after formation of a conductive layer, a coating of photosensitive material, e.g., photoresist, is disposed on top of the conductive layer. A contact mask is formed using a flexible optical waveguide having a surface area which covers all or a significant portion of the light-emitting panel. During formation of the waveguide, the cladding material is patterned to allow light to escape from the waveguide at selective locations corresponding to locations of the electrodes to be defined. The photoresist is exposed at the desired locations by light "leaking" from the waveguide, then the waveguide mask is removed. After the photoresist is cured and the unexposed resist is removed, the conductive material is selectively etched to form the electrodes at the desired locations.

Other features, advantages, and embodiments of the invention are set forth in part in the description that follows, and in part, will be obvious from this description, or may be learned from the practice of the invention.

BRIEF DESCRIPTION OF THE DRAWINGS

The foregoing and other features and advantages of this invention will become more apparent by reference to the following detailed description of the invention taken in conjunction with the accompanying drawings.

DETAILED DESCRIPTION OF THE PREFERRED EMBODIMENTS

As embodied and broadly described herein, the preferred embodiments of the present invention are directed to a novel method for making a light-emitting panel. In particular, preferred embodiments are directed to web fabrication processes for manufacturing light-emitting panels.

Figure 1:
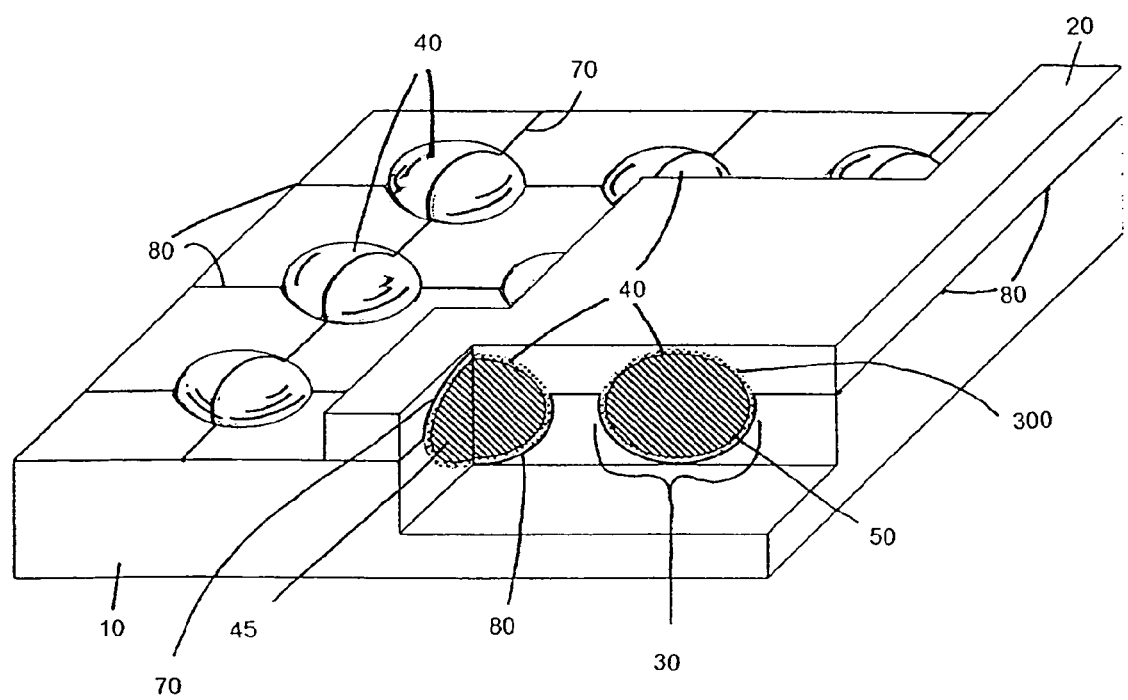
FIG. 1 is a perspective view of a portion of a light-emitting panel showing the basic socket structure of a socket formed from patterning a substrate, as disclosed in an embodiment of the present invention.

FIG. 1 illustrates an exemplary display panel in which a plurality of sphere-shaped micro-components 40 are embedded within a sandwich of dielectric layers consisting of first substrate 10 and second substrate 20. The first substrate 10 is formed from a flexible sheet material that is appropriate for web fabrication, such as polyester (e.g., Mylar®), polyimide (e.g., Kapton®), polypropylene, polyethylene, propylene, nylon or any polymer-based material possessing dielectric properties appropriate for use as an insulator between electrodes as needed for operation of a plasma display panel. Such electrical requirements are known to those of skill in the art. Second substrate 20 may be made from the same or similar dielectric material.

The first substrate 10 includes a plurality of sockets 30 adapted for retaining at least one micro-component 40. The sockets 30 may be disposed in any pattern, having uniform or non-uniform spacing between adjacent sockets. Patterns may include, but are not limited to, a uniform array, alphanumeric characters, symbols, icons, or pictures. Preferably, the sockets 30 are disposed in the first substrate 10 so that the distance between adjacent sockets 30 is approximately equal. Sockets 30 may also be disposed in groups such that the distance between one group of sockets and another group of sockets is approximately equal. This latter approach may be particularly relevant in color light-emitting panels, where each group of sockets represents a combination of the primary colors: red, green and blue.

Multiple micro-components may be disposed in a socket to provide increased luminosity and enhanced radiation transport efficiency. In a color light-emitting panel according to one embodiment of the present invention, a single socket supports three micro-components configured to emit red, green, and blue light, respectively. The micro-components 40 may be of any shape, including, but not limited to, spherical, cylindrical, and aspherical. In addition, it is contemplated that a micro-component 40 includes a micro-component placed or formed inside another structure, such as placing a spherical micro-component inside a cylindrical-shaped structure. In a color light-emitting panel according to an embodiment of the present invention, each cylindrical-shaped structure holds micro-components configured to emit a single color of visible light or multiple colors arranged red, green, blue, or in some other suitable color arrangement.

In one embodiment, the micro-components 40 are positioned in the sockets 30 of first substrate 10 by use of an ink-jet-type feeder which provides aligned placement of the micro-components 40. A number of methods of placing the micro-components in the sockets are disclosed in co-pending application Ser. No. 10/214,769, which is incorporated herein by reference in its entirety.

An adhesive or bonding agent, discussed below, may be applied to each micro-component to assist in placing/holding a micro-component 40 or plurality of micro-components in a socket 30. In an alternative embodiment, an electrostatic charge is placed on each micro-component and an electrostatic field is applied to each micro-component to assist in the placement of a micro-component 40 or plurality of micro-components in a socket 30. This technique, known as "electrostatic sheet transfer" ("EST") is described in the aforementioned co-pending application Ser. No. 10/214,769. Applying an electrostatic charge to the micro-components also helps avoid agglomeration among the plurality of micro-components. In one embodiment of the present invention, an electron gun may be used to place an electrostatic charge on each micro-component, then one electrode disposed proximate to each socket 30 is energized to provide the opposing electrostatic field required to attract the electrostatically charged micro-component.

In order to assist in placing/holding a micro-component 40 or plurality of micro-components in a socket 30, a socket 30 may contain a bonding agent or an adhesive. The bonding agent or adhesive, typically an electrically-conductive epoxy material which is filled with, for example, silver, copper, aluminum, or other conductor, may be applied to the inside of the socket 30 by differential stripping, lithographic process, sputtering, laser deposition, chemical deposition, vapor deposition, or preferably, by deposition using ink jet technology. One skilled in the art will recognize that other methods of coating the inside of the socket 30 may be used.

In its most basic form, each micro-component 40 includes a shell 50 filled with a plasma-forming gas or gas mixture 45. Any suitable gas or gas mixture 45 capable of ionization may be used as the plasma-forming gas, including, but not limited to, krypton, xenon, argon, neon, oxygen, helium, mercury, and mixtures thereof. In fact, any noble gas could be used as the plasma-forming gas, including, but not limited to, noble gases mixed with cesium or mercury. Further, rare gas halide mixtures such as xenon chloride, xenon fluoride and the like are also suitable plasma-forming gases. Rare gas halides are efficient radiators having radiating wavelengths over the approximate range of 190 nm to 350 nm, i.e. longer than that of pure xenon (147 to 170 nm). Using compounds such as xenon chloride that radiates near 310 nm results in an overall quantum efficiency gain, i.e., a factor of two or more, given by the mixture ratio. Still further, in another embodiment of the present invention, rare gas halide mixtures are also combined with other plasma-forming gases as listed above. This description is not intended to be limiting. One skilled in the art would recognize other gases or gas mixtures that could also be used. In a color display, the plasma-forming gas or gas mixture 45 is chosen so that during ionization the gas will produce a specific wavelength of light corresponding to a desired color. For example, neon-argon emits red light, xenon-oxygen emits green light, and krypton-neon emits blue light. While a plasma-forming gas or gas mixture 45 is used in a preferred embodiment, any other material capable of luminescing is also contemplated, such as an electro-luminescent material, organic light-emitting diodes (OLEDs), or an electrophoretic material.

The shell 50 may be made from a wide assortment of materials, including, but not limited to, silicates, polypropylene, glass, any polymeric-based material, magnesium oxide and quartz and may be of any suitable size. The shell 50 may have a diameter ranging from micrometers to centimeters as measured across its minor axis, with virtually no limitation as to its size as measured across its major axis. For example, a cylindrical-shaped micro-component may be only 100 microns in diameter across its minor axis, but may be hundreds of meters long across its major axis. In a preferred embodiment, the outside diameter of the shell, as measured across its minor axis, is from 100 microns to 300 microns. In addition, the shell thickness may range from micrometers to millimeters, with a preferred thickness from 1 micron to 10 microns.

When a sufficiently large voltage is applied across the micro-component the gas or gas mixture ionizes forming plasma and emitting radiation. The potential required to initially ionize the gas or gas mixture inside the shell 50 is governed by Paschen's Law and is closely related to the pressure of the gas inside the shell. In the present invention, the gas pressure inside the shell 50 ranges from tens of torrs to several atmospheres. In a preferred embodiment, the gas pressure ranges from 100 torr to 700 torr. The size and shape of a micro-component 40, and the type and pressure of the plasma-forming gas contained therein, influence the performance and characteristics of the light-emitting panel and are selected to optimize the panel's efficiency of operation.

There are a variety of coatings 300 and dopants that may be added to a micro-component 40 that also influence the performance and characteristics of the light-emitting panel. The coatings 300 may be applied to the outside or inside of the shell 50, and may either partially or fully coat the shell 50. Types of outside coatings include, but are not limited to, coatings used to convert UV light to visible light (e.g. phosphor), coatings used as reflecting filters, and coatings used as band-gap filters. Types of inside coatings include, but are not limited to, coatings used to convert UV light to visible light (e.g. phosphor), coatings used to enhance secondary emissions and coatings used to prevent erosion. Those skilled in the art will recognize that other coatings may also be used. The coatings 300 may be applied to the shell 50 by differential stripping, lithographic processes, sputtering, laser deposition, chemical deposition, vapor deposition, or deposition using ink jet technology. In a preferred embodiment, the coating is applied by immersing the micro-components in a slurry of phosphor particles, similar to the procedures used in the manufacture of fluorescent lamps, so that the particles adhere to the outer surface of the micro-component. One skilled in the art will recognize that other methods of coating the inside and/or outside of the shell 50 may be used. Types of dopants include, but are not limited to, dopants used to convert UV light to visible light (e.g. phosphor), dopants used to enhance secondary emissions and dopants used to provide a conductive path through the shell 50. The dopants are added to the shell 50 by any suitable technique known to one skilled in the art, including ion implantation. It is contemplated that any combination of coatings and dopants may be added to a micro-component 40. Alternatively, or in combination with the coatings and dopants that may be added to a micro-component 40, a variety of coatings may be coated on the inside of a socket 30. These coatings include, but are not limited to, coatings used to convert UV light to visible light, coatings used as reflecting filters, and coatings used as band-gap filters.

In an embodiment of the light emitting panel, when a micro-component is configured to emit UV light, the UV light is converted to visible light by at least partially coating the inside the shell 50 with phosphor, at least partially coating the outside of the shell 50 with phosphor, doping the shell 50 with phosphor and/or coating the inside of a socket 30 with phosphor. In a color panel, according to an embodiment of the present invention, colored phosphor is chosen so the visible light emitted from alternating micro-components is colored red, green and blue, respectively. By combining these primary colors at varying intensities, all colors can be formed. It is contemplated that other color combinations and arrangements may be used. In another embodiment for a color light-emitting panel, the UV light is converted to visible light by disposing a single colored phosphor on the micro-component 40 and/or on the inside of the socket 30. Colored filters may then be alternatingly applied over each socket 30 to convert the visible light to colored light of any suitable arrangement, for example red, green and blue. By coating all the micro-components with a single colored phosphor and then converting the visible light to colored light by using at least one filter applied over the top of each socket, micro-component placement is made less complicated and the light-emitting panel is more easily configurable.

Additional coatings may be applied or modifications made to the micro-component to enhance performance, for example, by increasing luminosity and radiation transport efficiency, and to permit construction of a DC light-emitting panel. Luminousity can be improved by at least partially coating the micro-component with a secondary emission enhancement material such as magnesium oxide and thulium oxide. Alternatively or in conjunction with the coating, the shell can be doped with a secondary emission enhancement material. The micro-component can also be coated with or have a doped shell to enhance emission and/or radiation transport with reflective or conductive materials. Doping the shell 50 with a conductive material such as silver, gold, platinum or aluminum provides a direct conductive path to the gas or gas mixture contained in the shell. Also, an index matching material may be used to select a pre-determined emission wavelength, i.e., providing a bandpass filter.

The size and shape of the socket 30 influence the performance and characteristics of the light-emitting panel and are selected to optimize the panel's efficiency of operation. In addition, socket geometry may be selected based on the shape and size of the micro-component to optimize the surface contact between the micro-component and the socket and/or to ensure connectivity of the micro-component and any electrodes disposed within the socket. Further, the size and shape of the sockets 30 may be chosen to optimize photon generation and provide increased luminosity and radiation transport efficiency. For example, the size and shape may be chosen to provide a field of view with an angle that can be made wider or narrower as needed for a specific application. That is to say, the cavity may be sized, for example, so that its depth subsumes a micro-component deposited in a socket, or it may be made shallow so that a micro-component is only partially disposed within a socket. Alternatively, in another embodiment of the present invention, the field of view may be set to a specific angle by disposing on the second substrate at least one optical lens. The lens may cover the entire second substrate or, in the case of multiple optical lenses, arranged so as to correspond with each socket. In another embodiment, the optical lens or optical lenses are configurable to adjust the field of view of the light-emitting panel.

Figure 3A:
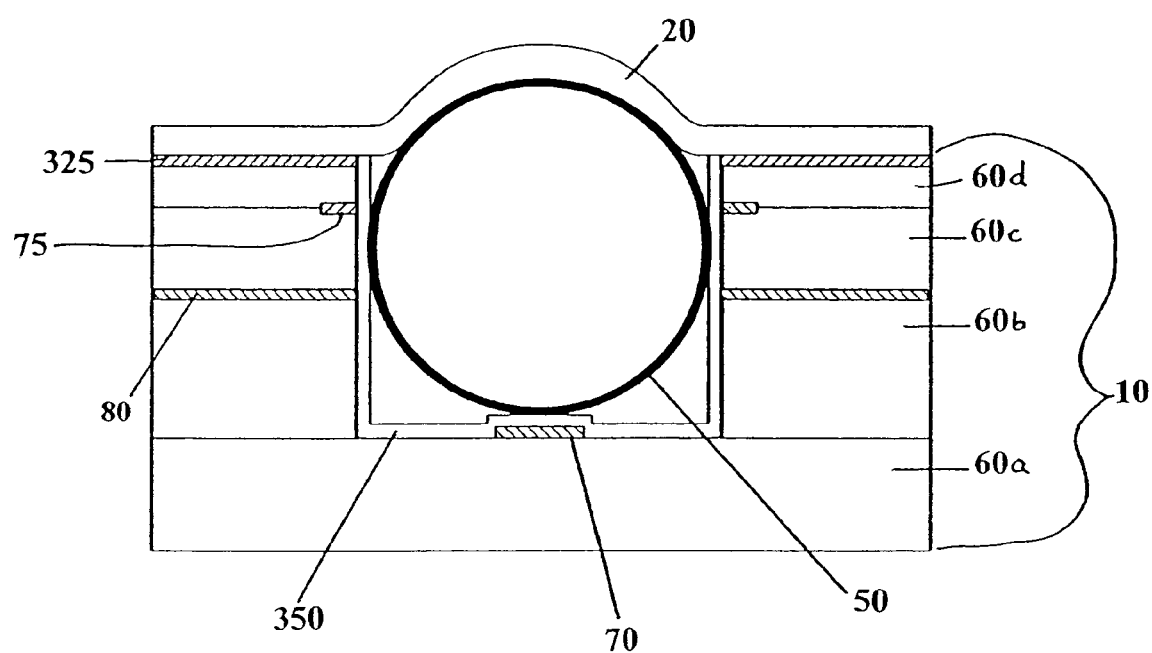
FIG. 3a is a diagrammatic cross-sectional view of a portion of an embodiment of the light-emitting panel with the electrodes having a mid-plane configuration.

In an embodiment for a method of making a light-emitting panel including a plurality of sockets, a cavity is formed, or patterned, in a substrate 10 to create a basic socket 30, such as illustrated in FIG. 1. The cavity may be formed in any suitable shape and size by any combination of physically, mechanically, thermally, electrically, optically, or chemically deforming the substrate. Disposed proximate to, and/or in, each socket 30 may be a variety of enhancement materials 325, as shown in FIG. 3a. The enhancement materials 325 include, but are not limited to, anti-glare coatings, touch sensitive surfaces, contrast enhancement (black mask) coatings, protective coatings, transistors, integrated-circuits, semiconductor devices, inductors, capacitors, resistors, control electronics, drive electronics, diodes, pulse-forming networks, pulse compressors, pulse transformers, and tuned-circuits.

Still referring to FIG. 3a, a socket 30 is formed by stacking a plurality of material layers 60a–d to form the first substrate, disposing at least one electrode either directly on the top of the first substrate, within the material layers or any combination thereof, and selectively removing a portion of the material layers 60a–d to create a cavity. The material layers 60a–d include any combination, in whole or in part, of dielectric materials, metals, and enhancement materials 325, as discussed above. The placement of the material layers 60 may be accomplished by any transfer process, photolithography, sputtering, laser deposition, chemical deposition, vapor deposition, xerographic-type processes, plasma deposition, or deposition using ink jet technology. One of general skill in the art will recognize other appropriate methods of disposing a plurality of material layers on a substrate. The socket 30 may be formed in the combination of layers 60a–d using any of a variety of methods on the layers, either individually or combined, including, but not limited to, wet or dry etching, photolithography, laser heat treatment, thermal form, mechanical punch, embossing, stamping-out, drilling, electroforming or by dimpling.

Figure 5:
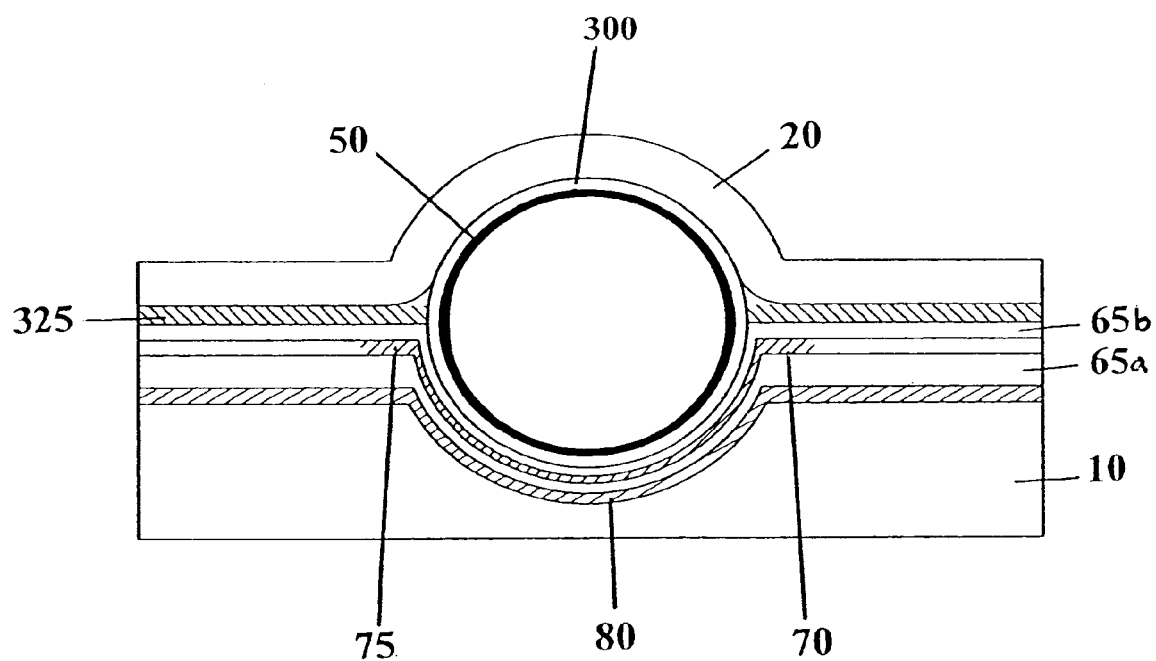
FIG. 5 is a diagrammatic cross-sectional view of a portion of an embodiment of the light-emitting panel with the electrodes having a co-planar configuration.

Using FIG. 5 to illustrate, in an alternate method of forming a socket 30, a cavity 55 is formed in a first substrate 10, then a plurality of material layers 65a,b is disposed over the first substrate 10 so that the material layers 65a,b conform to the cavity 55. At least one electrode is formed on the first substrate 10, within the material layers 65, or any combination thereof. In the example of FIG. 5, electrode 80 is formed on the first substrate, while electrodes 70 and 75 are disposed within the layers. The cavity may be formed in any suitable shape and size by any combination of physically, mechanically, thermally, electrically, optically, or chemically deforming the substrate. The material layers 65a,b include any combination, in whole or in part, of dielectric materials, metals, and enhancement materials 325, as described previously. The placement of the material layers 65a,b may be accomplished by any transfer process, photolithography, sputtering, laser deposition, chemical deposition, vapor deposition, xerographic-type processes, plasma deposition, coating with a liquid or deposition using ink jet technology. One of general skill in the art will recognize other appropriate methods of disposing a plurality of material layers on a substrate.

In yet another alternative method of forming a socket, at least one electrode is disposed on the first substrate, within the material layers, or any combination thereof. Each of the material layers includes a preformed aperture that extends through the entire material layer. The apertures may be of the same size or may be of different sizes, e.g., they may be graduated in size to create the socket with a tapered or curved profile. The plurality of material layers are sequentially disposed on top of the first substrate with the apertures in alignment thereby forming a cavity. The material layers include any combination, in whole or in part, of dielectric materials, metals, and enhancement materials, as described previously. The placement of the material layers may be accomplished by any transfer process, photolithography, sputtering, laser deposition, chemical deposition, vapor deposition, xerographic-type processes, plasma deposition, or deposition using ink jet technology. One of general skill in the art will recognize other appropriate methods of disposing a plurality of material layers on a substrate.

In the above-described methods of making a socket in a light-emitting panel, disposed in, or proximate to, each socket may be at least one enhancement material. As stated above the enhancement material 325 may include, but is not limited to, anti-glare coatings, touch sensitive surfaces, contrast enhancement (black mask) coatings, protective coatings, transistors, integrated-circuits, semiconductor devices, inductors, capacitors, resistors, control electronics, drive electronics, diodes, pulse-forming networks, pulse compressors, pulse transformers, and tuned-circuits. In a preferred embodiment of the present invention, the enhancement materials may be disposed in, or proximate to each socket by any transfer process, photolithography, sputtering, laser deposition, chemical deposition, vapor deposition, xerographic-type processes, plasma deposition, deposition using ink jet technology, or mechanical means. In another embodiment of the present invention, a method for making a light-emitting panel includes disposing at least one electrical enhancement (e.g. the transistors, integrated-circuits, semiconductor devices, inductors, capacitors, resistors, control electronics, drive electronics, diodes, pulse-forming networks, pulse compressors, pulse transformers, and tuned-circuits), in, or proximate to, each socket by suspending the at least one electrical enhancement in a liquid and flowing the liquid across the first substrate. As the liquid flows across the substrate the at least one electrical enhancement will settle in each socket. It is contemplated that other substances or means may be use to move the electrical enhancements across the substrate. One such means may include, but is not limited to, using air to move the electrical enhancements across the substrate. In another embodiment of the present invention the socket is of a corresponding shape to the at least one electrical enhancement such that the at least one electrical enhancement self-aligns with the socket.

The electrical enhancements may be used in a light-emitting panel for a number of purposes including, but not limited to, lowering the ionization potential of the plasma-forming gas in a micro-component, lowering the voltage required to sustain/erase the ionization charge in a micro-component, increasing the luminosity and/or radiation transport efficiency of a micro-component, and augmenting the frequency at which a micro-component is activated or illuminated. In addition, the electrical enhancements may be used in conjunction with the light-emitting panel driving circuitry to alter the power requirements necessary to drive the light-emitting panel. For example, a tuned-circuit may be used in conjunction with the driving circuitry to allow a DC power source to power an AC-type light-emitting panel. In an embodiment of the present invention, a controller is provided that is connected to the electrical enhancements and capable of controlling their operation. Having the ability to individually control the electrical enhancements at each pixel/subpixel provides a means by which the characteristics of individual micro-components may be altered/corrected after fabrication of the light-emitting panel. These characteristics include, but are not limited to, luminosity and the frequency at which a micro-component is lit. One skilled in the art will recognize other uses for electrical enhancements disposed in, or proximate to, each socket in a light-emitting panel.

The electrical potential necessary to energize a micro-component 40 is supplied via at least two electrodes. In a general configuration, the light-emitting panel includes a plurality of electrodes, wherein at least two electrodes are adhered to either the first substrate or the second substrate, or at least one electrode is adhered to each of the first substrate and the second substrate and wherein the electrodes are arranged so that voltage applied to the electrodes causes one or more micro-components to emit radiation. In another general configuration, a light-emitting panel includes a plurality of electrodes, wherein at least two electrodes are arranged so that voltage supplied to the electrodes causes one or more micro-components to emit radiation throughout the field of view of the light-emitting panel without crossing either of the electrodes.

In an embodiment where the sockets 30 are patterned on the first substrate 10 so that the sockets are formed in the first substrate, at least two electrodes may be disposed on the first substrate 10, the second substrate 20, or any combination thereof. In the exemplary embodiment shown in FIG. 1, a sustain electrode 70 is disposed on or within the second substrate 20 and an address electrode 80 is disposed on or within the first substrate 10. As illustrated, address electrode 80 is positioned in the first substrate 10 so that it is at least partly disposed within the socket.

Methods for distributing the micro-components into the sockets include dispensing the micro-components using a placement tool, an ink jet-type printer, or a gravity-fed drop tower which is aligned with the sockets in the substrate. Alternatively, the substrate may be passed through one or more vibratory, e.g., ultrasonic, shaker baths containing an excess plurality of micro-components, i.e., a much larger number of micro-components than are needed to fill the available positions on the substrate. Such shakers are well known in the art and may include orbital shakers and other vibratory movements. The shaking causes the micro-components to be dispersed across the surface of the substrate so that a micro-component is disposed within each of the sockets. A further discussion of different methods for placement of the plurality of micro-components is provided in the aforementioned co-pending application Ser. No. 10/214,769.

Figure 2A:
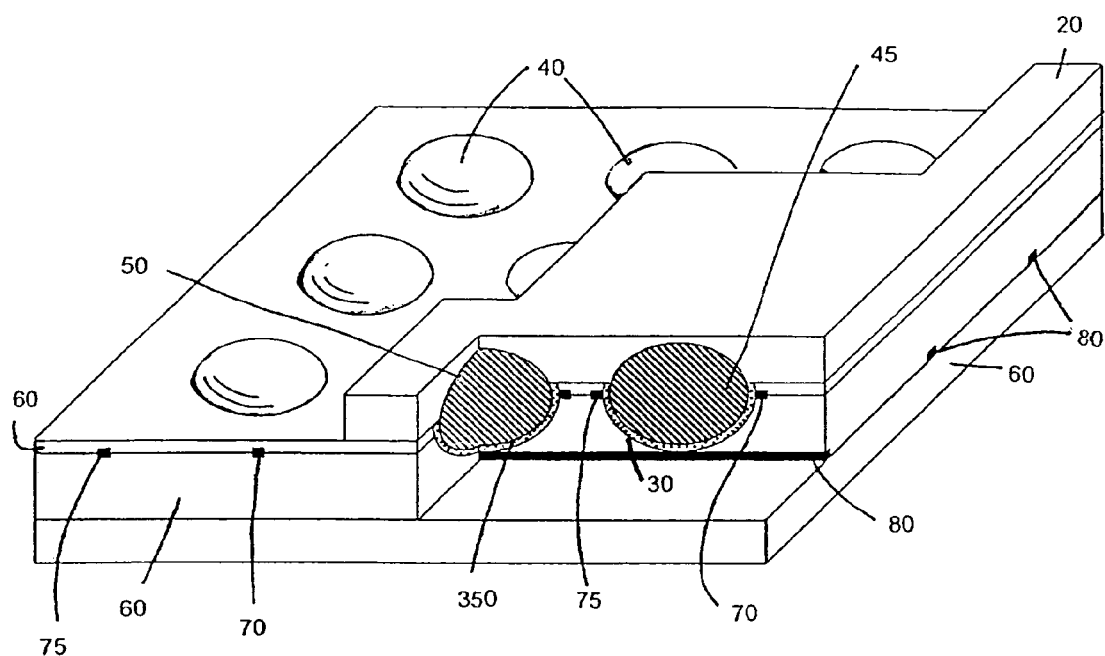
FIG. 2a is a perspective view of a portion of a light-emitting panel, partially cut-away, to reveal micro-components and electrodes.
Figure 2B:
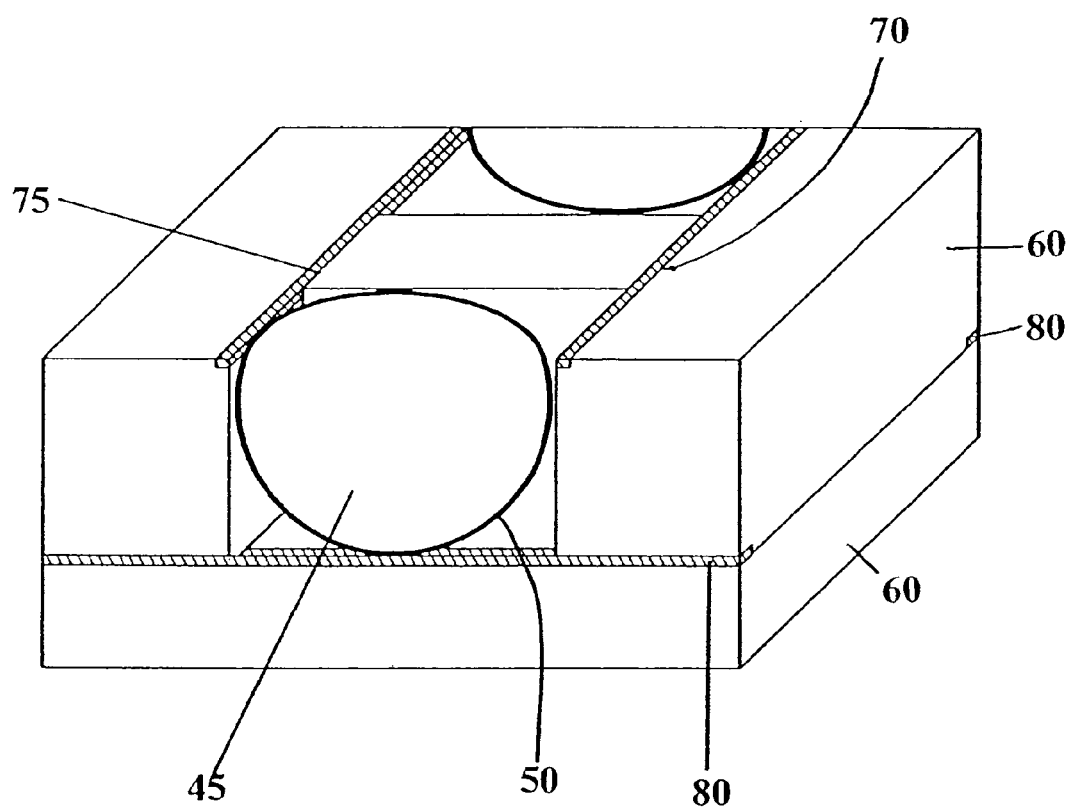
FIG. 2b is a detail view of the embodiment of FIG. 2a with upper dielectric layers cut away to reveal the co-planar sustaining electrodes.
Figure 3B:
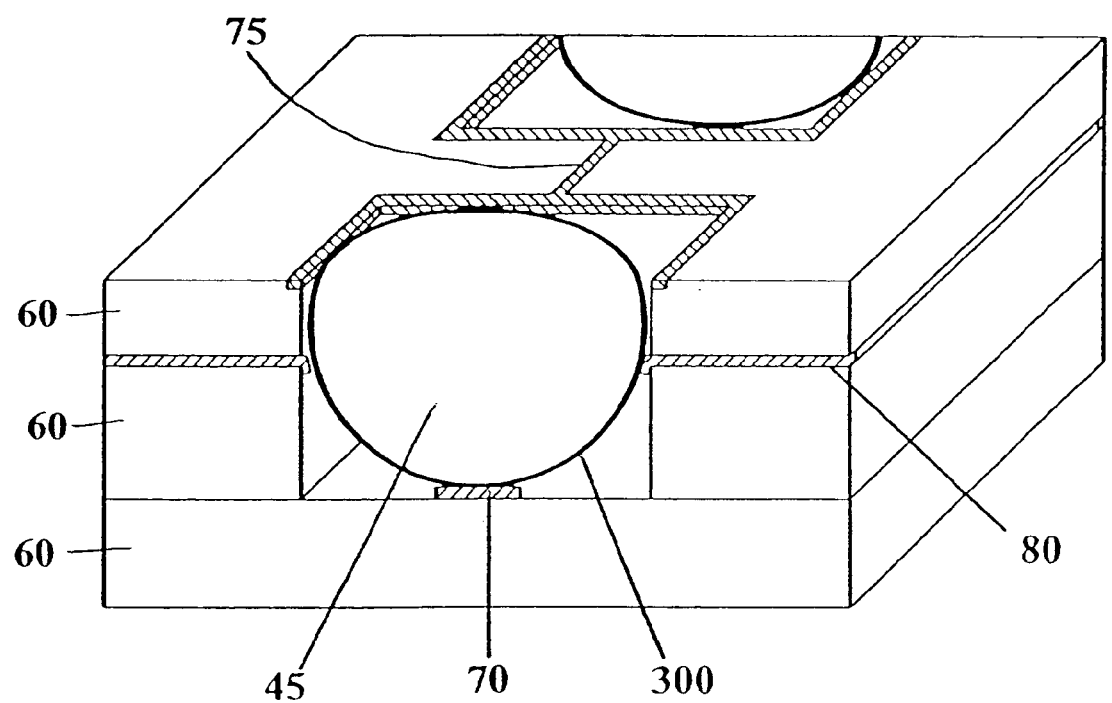
FIG. 3b is a perspective view of the embodiment of FIG. 3a with the upper dielectric layer cut away to reveal the uppermost sustain electrode.
Figure 4:
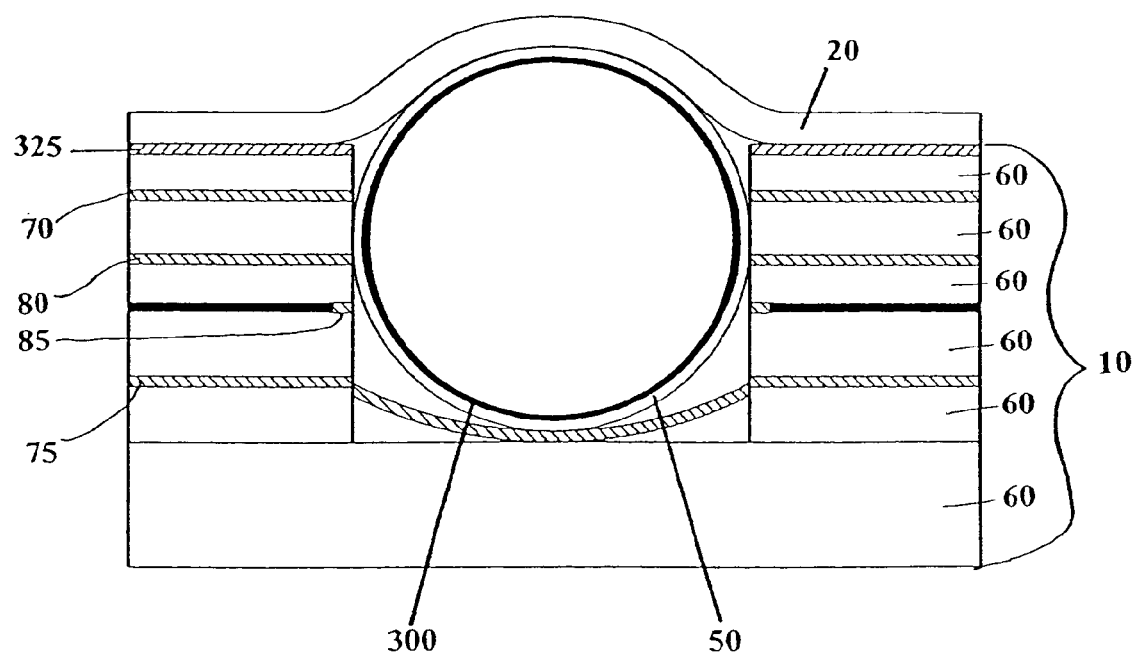
FIG. 4 is a diagrammatic cross-sectional view of a portion of an embodiment of the light-emitting panel with the electrodes having a configuration with two sustain and two address electrodes, where the address electrodes are between the two sustain electrodes.

In an embodiment of the light emitting panel where the first substrate 10 includes a plurality of material layers 60 and the sockets 30 are formed within the material layers, at least two electrodes may be disposed on the first substrate 10, disposed within the material layers 60, disposed on the second substrate 20, or any combination thereof. In one embodiment, as shown in FIG. 2a, a first address electrode 80 is disposed within the material layers 60, a first sustain electrode 70 is disposed within the material layers 60, and a second sustain electrode 75 is disposed within the material layers 60, such that the first sustain electrode and the second sustain electrode are in a co-planar configuration. FIG. 2b is a cut-away of FIG. 2a showing the arrangement of the co-planar sustain electrodes 70 and 75. In another embodiment, as shown in FIG. 3a, a first sustain electrode 70 is disposed on the first substrate 10, a first address electrode 80 is disposed within the material layers 60, and a second sustain electrode 75 is disposed within the material layers 60, such that the first address electrode is located between the first sustain electrode and the second sustain electrode in a mid-plane configuration. FIG. 3b is a cut-away of FIG. 3a showing the first sustain electrode 70. As seen in FIG. 4, in a preferred embodiment of the light emitting panel, a first sustain electrode 70 is disposed within the material layers 60, a first address electrode 80 is disposed within the material layers 60, a second address electrode 85 is disposed within the material layers 60, and a second sustain electrode 75 is disposed within the material layers 60, such that the first address electrode and the second address electrode are located between the first sustain electrode and the second sustain electrode.

Figure 6:
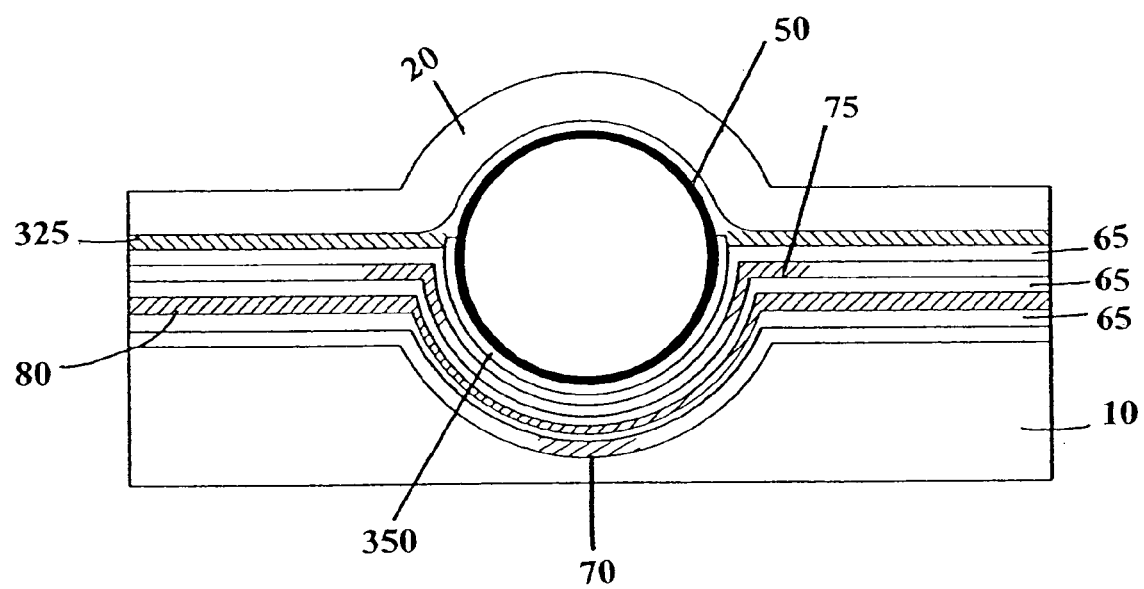
FIG. 6 is a diagrammatic cross-sectional view of a portion of an embodiment of the light-emitting panel with the electrodes having a mid-plane configuration.
Figure 7:
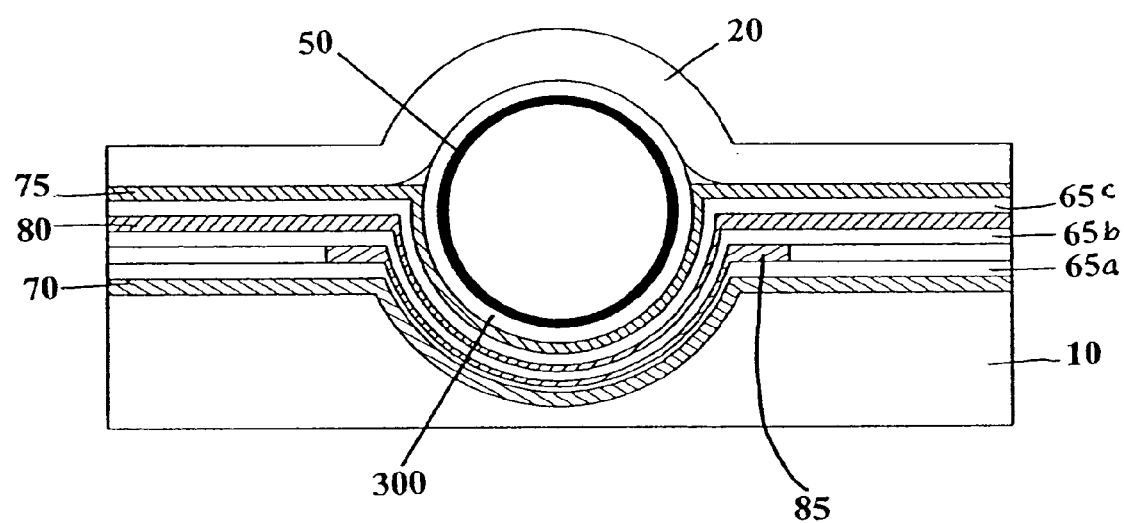
FIG. 7 is a diagrammatic cross-sectional view of a portion of an embodiment of the light-emitting panel with the electrodes having a configuration with two sustain and two address electrodes, where the address electrodes are between the two sustain electrodes.

In an embodiment where a cavity 55 is patterned on the first substrate 10 and a plurality of material layers 65 are disposed on the first substrate 10 so that the material layers conform to the cavity 55, at least two electrodes may be disposed on the first substrate 10, at least partially disposed within the material layers 65, disposed on the second substrate 20, or any combination thereof. In one embodiment, as shown in FIG. 5, a first address electrode 80 is disposed on the first substrate 10, a first sustain electrode 70 is disposed within the material layers 65, and a second sustain electrode 75 is disposed within the material layers 65, such that the first sustain electrode and the second sustain electrode are in a co-planar configuration. In another embodiment, as shown in FIG. 6, a first sustain electrode 70 is disposed on the first substrate 10, a first address electrode 80 is disposed within the material layers 65, and a second sustain electrode 75 is disposed within the material layers 65, such that the first address electrode is located between the first sustain electrode and the second sustain electrode in a mid-plane configuration. As seen in FIG. 7, in a preferred embodiment of the present invention, a first sustain electrode 70 is disposed on the first substrate 10, a first address electrode 80 is disposed within the material layers 65, a second address electrode 85 is disposed within the material layers 65, and a second sustain electrode 75 is disposed within the material layers 65, such that the first address electrode and the second address electrode are located between the first sustain electrode and the second sustain electrode.

Figure 11:
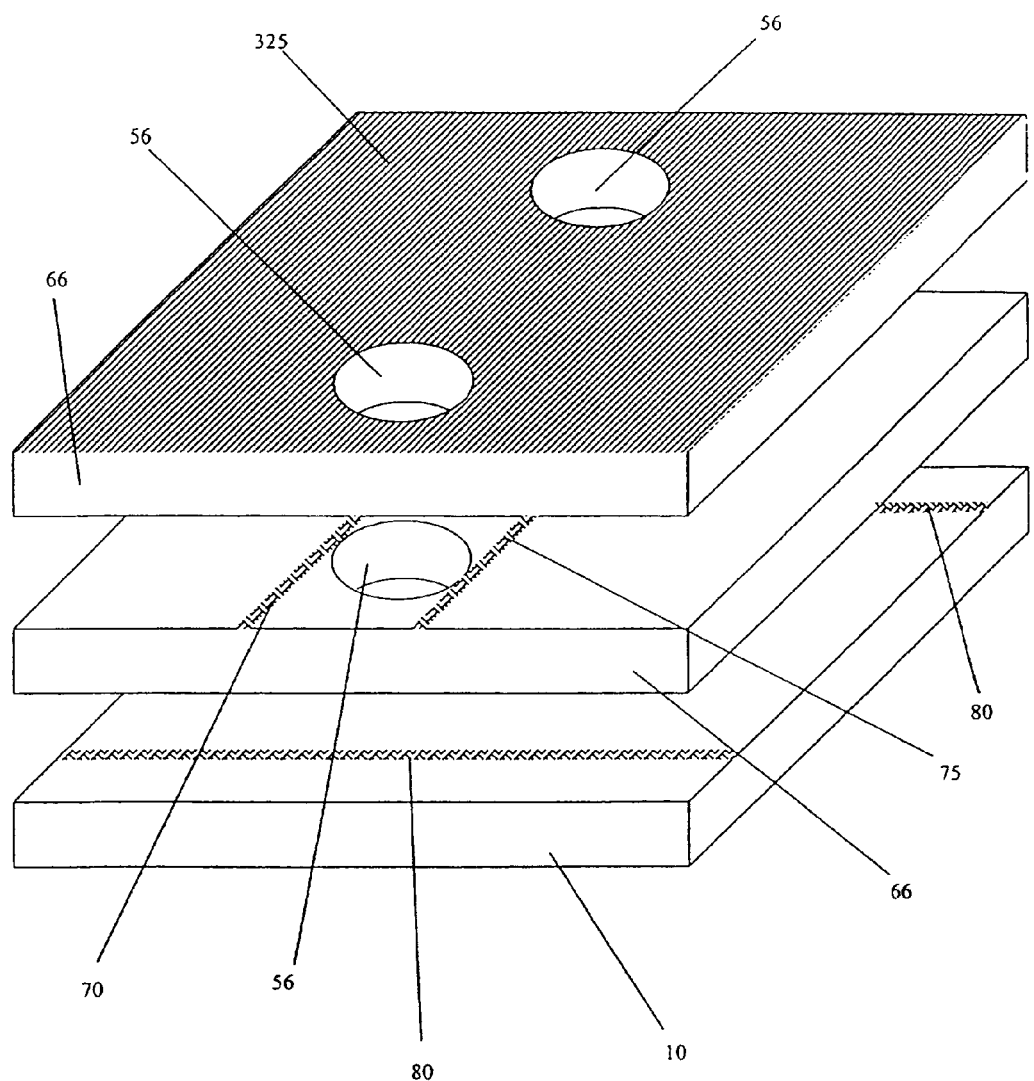
FIG. 11 is an exploded perspective view of a portion of a light-emitting panel showing the basic socket structure of a socket formed by disposing a plurality of material layers with aligned apertures on a substrate with the electrodes having a co-planar configuration.
Figure 12:
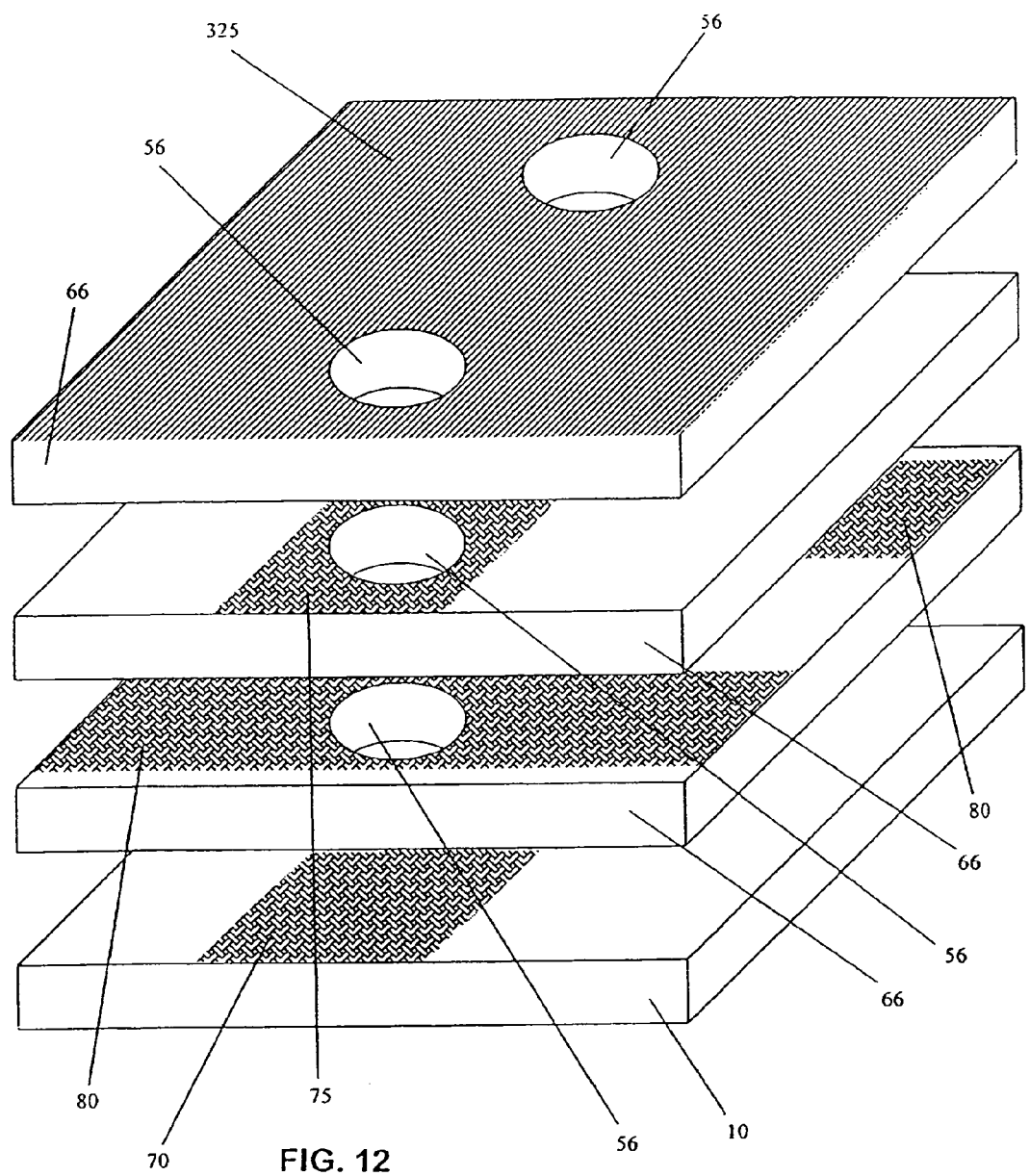
FIG. 12 shows an exploded perspective view of a portion of a light-emitting panel showing the basic socket structure of a socket formed by disposing a plurality of material layers with aligned apertures on a substrate with the electrodes having a mid-plane configuration.
Figure 13:
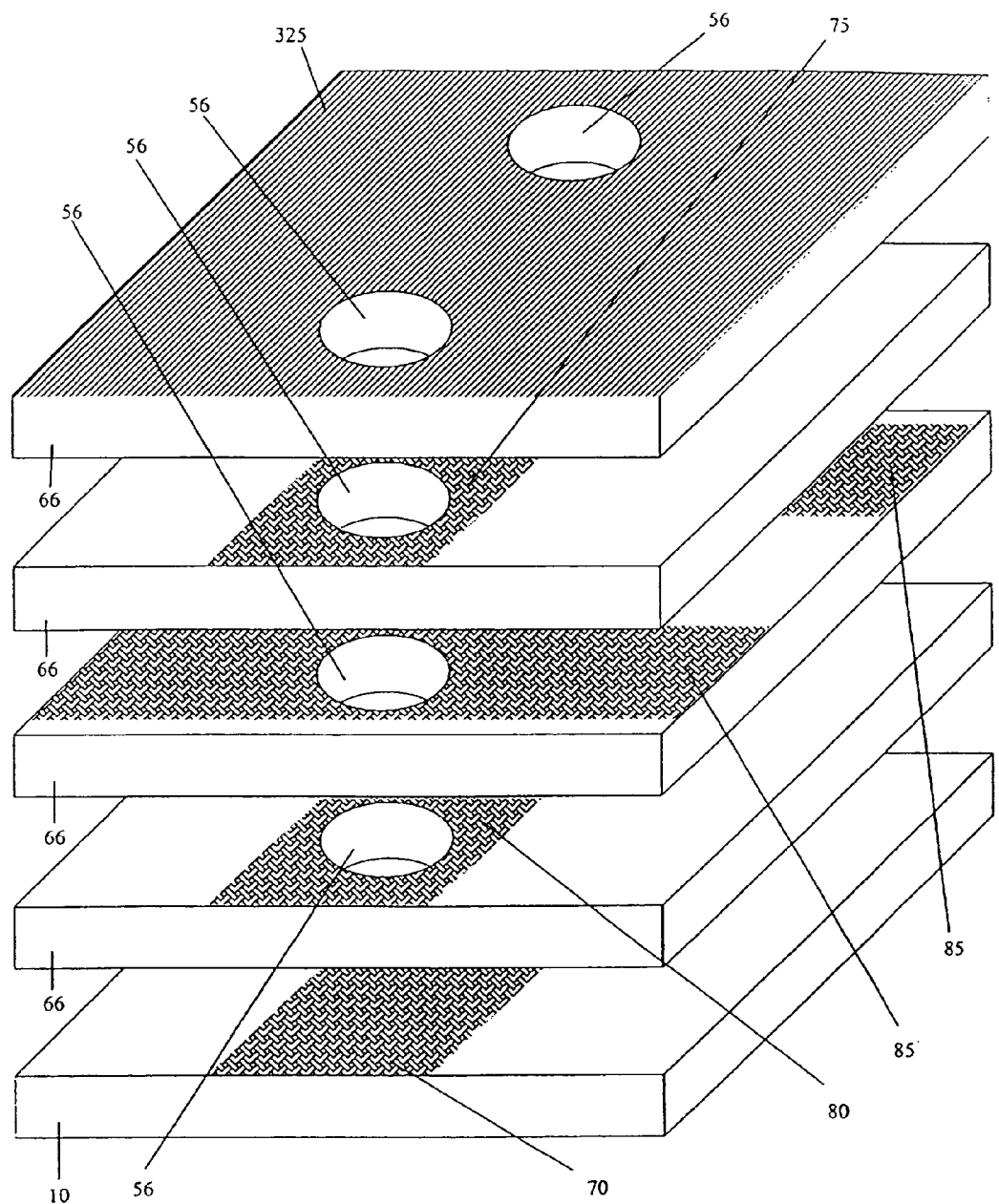
FIG. 13 shows an exploded view of a portion of a light-emitting panel showing the basic socket structure of a socket formed by disposing a plurality of material layers with aligned apertures on a substrate with electrodes having a configuration with two sustain and two address electrodes, where the address electrodes are between the two sustain electrodes.

In an embodiment where a plurality of material layers 66 with aligned apertures 56 are disposed on a first substrate 10 thereby creating the cavities 55, at least two electrodes may be disposed on the first substrate 10, at least partially disposed within the material layers 65, disposed on the second substrate 20, or any combination thereof. In one embodiment, as shown in FIG. 11, a first address electrode 80 is disposed on the first substrate 10, a first sustain electrode 70 is disposed within the material layers 66, and a second sustain electrode 75 is disposed within the material layers 66, such that the first sustain electrode and the second sustain electrode are in a co-planar configuration. In another embodiment, as shown in FIG. 12, a first sustain electrode 70 is disposed on the first substrate 10, a first address electrode 80 is disposed within the material layers 66, and a second sustain electrode 75 is disposed within the material layers 66, such that the first address electrode is located between the first sustain electrode and the second sustain electrode in a mid-plane configuration. As seen in FIG. 13, in a preferred embodiment of the light emitting panel, a first sustain electrode 70 is disposed on the first substrate 10, a first address electrode 80 is disposed within the material layers 66, a second address electrode 85 is disposed within the material layers 66, and a second sustain electrode 75 is disposed within the material layers 66, such that the first address electrode and the second address electrode are located between the first sustain electrode and the second sustain electrode.

The specification, above, has described, among other things, various components of a light-emitting panel and methodologies to make those components and to make a light-emitting panel. In an embodiment of the present invention, it is contemplated that those components may be manufactured and those methods for making may be accomplished as part of web fabrication process for manufacturing light-emitting panels. In another embodiment of the present invention, a web fabrication process for manufacturing light-emitting panels includes the steps of providing a first substrate, disposing micro-components on the first substrate, disposing a second substrate on the first substrate so that the micro-components are sandwiched between the first and second substrates, and dicing the first and second substrate "sandwich" to form individual light-emitting panels. In another embodiment, the first and second substrates are provided as rolls of material. A plurality of sockets may either be preformed on the first substrate or may be formed in and/or on the first substrate as part of the web fabrication process. Likewise, the first and second substrates may be pre-formed so that the first substrate, the second substrate or both substrates include a plurality of electrodes. Alternatively, a plurality of electrodes may be disposed on or within the first substrate, on or within the second substrate, or on and within both the first substrate and second substrate as part of the web fabrication process. It should be noted that where suitable, fabrication steps may be performed in any order. It should also be noted that the micro-components may be preformed or may be formed as part of the web fabrication process. In another embodiment, the web fabrication process is performed as a continuous high-speed inline process with the ability to manufacture light-emitting panels at a rate faster than light-emitting panels manufactured as part of batch process.

Figure 8:
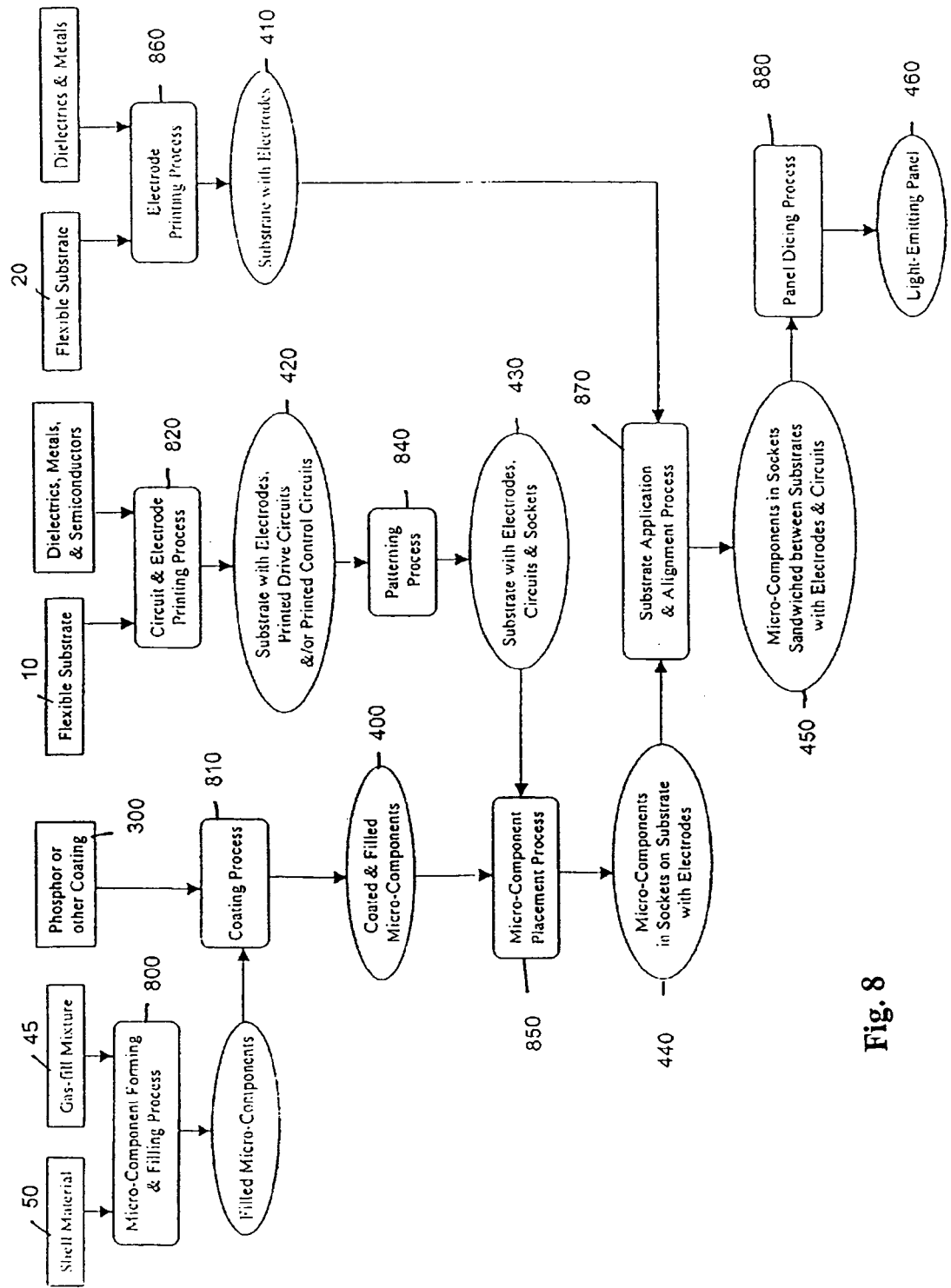
FIG. 8 is a flowchart of a first embodiment of a web fabrication method for manufacturing light-emitting displays according to the present invention.
Figure 9:
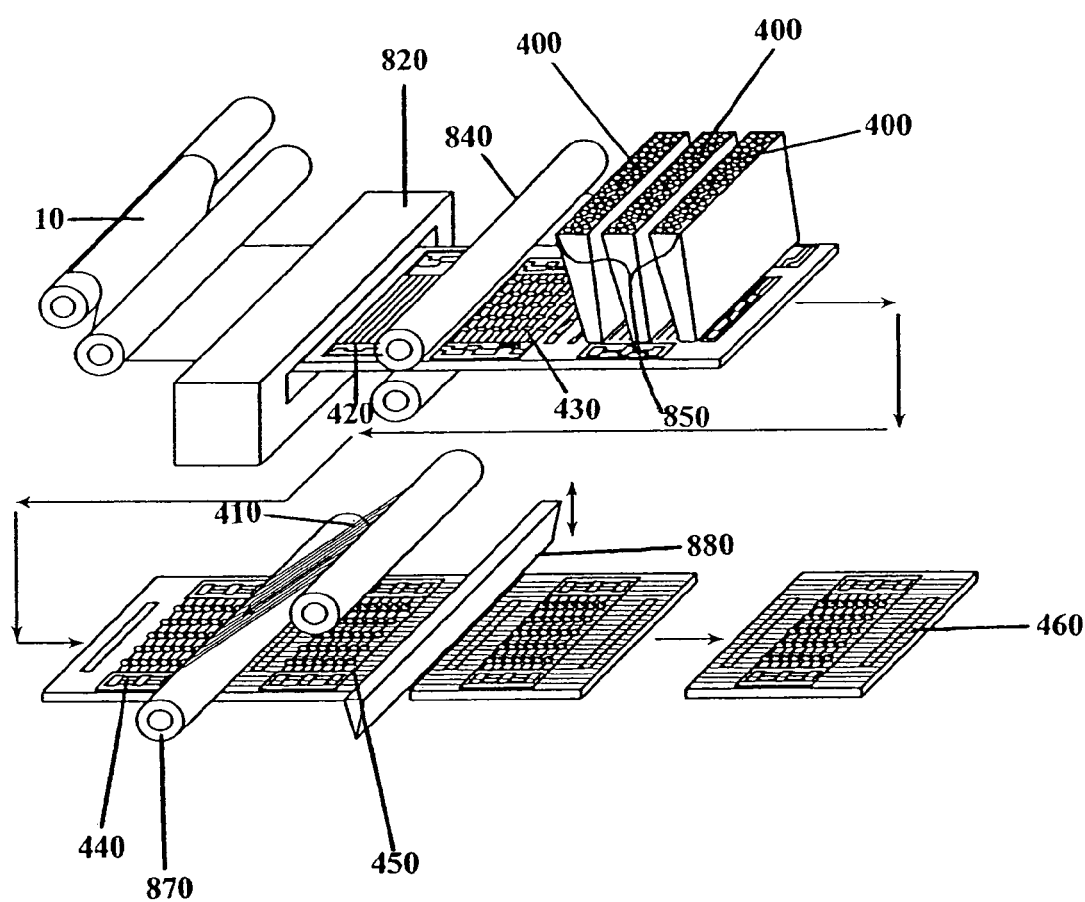
FIG. 9 is a graphical representation of a web fabrication process for manufacturing light-emitting panels according to the first embodiment of the web fabrication method.

As illustrated in FIGS. 8 and 9, in an embodiment of the present invention, the web fabrication process includes the following process steps: First, a micro-component forming process 800 is performed to create the micro-component shells 50 and fill the micro-components with plasma-forming gas 45. A micro-component coating process 810 follows in which the micro-components are coated with phosphor 300 or any other suitable coatings, producing a plurality of coated and filled micro-components 400. In a preferred embodiment, coating of the micro-components is achieved by immersing the micro-components in a slurry of phosphor particles, allowing the phosphor particles to adhere to the outer surface. Afterwards, the micro-components are processed through a curing step to remove the solvents that were used to create the slurry. A circuit and electrode printing process 820 prints at least one electrode and any needed driving and control circuitry on a first substrate 420. Patterning process 840 is performed to create a plurality of cavities on a first substrate to provide a plurality of sockets 430. Generally, this step involves applying pressure and possibly heat to deform the substrate material and create a plurality of dimples in the substrate. Micro-component placement process 850 places at least one coated and filled micro-component 400 in each socket 430, resulting in a first substrate assembly 440 comprising micro-components 400 in sockets 430 on the first substrate 10. If required, an electrode printing process 860 prints at least one electrode on a second flexible substrate 20 to produce a second substrate with electrodes 410. Second substrate application and alignment process 870 aligns the second substrate 410 over the first substrate assembly 440 so that the micro-components are sandwiched between the first substrate and the second substrate as assembly 450. Panel dicing process 880 cuts through the assembly 450 to yield individual light-emitting panels 460.

Figure 10:
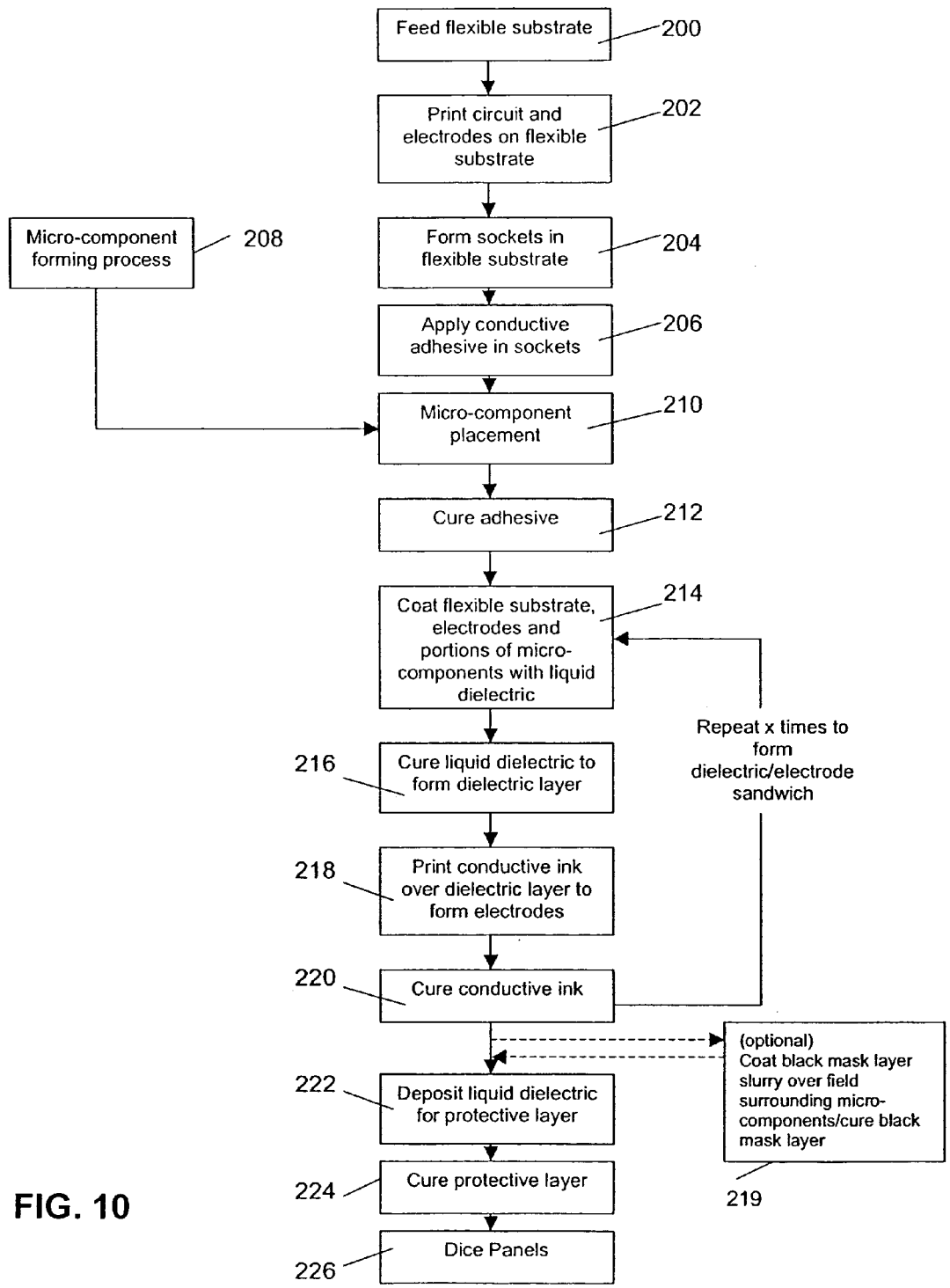
FIG. 10 is a flow diagram of a second embodiment of a web fabrication method according to the present invention.

The process flow for an alternate embodiment of the web fabrication method is illustrated in FIG. 10. As in the previously-described embodiment, the first substrate is a flexible dielectric material, which in step 200 is fed from a payout reel, to which a plurality of micro-components is applied, either by aligned placement with sockets (dimples) and/or adhesive spots formed in/on the first substrate, or by passing the first substrate with adhesive spots through a shaker bath filled with micro-components, as discussed above.

According to the exemplary process flow, electrodes and other circuitry are printed on the flexible substrate (step 202), typically using an ink-jet process, then sockets are formed (204). It should be noted that these steps may be performed in reverse order, i.e., the sockets may be formed prior to patterning the electrodes. Conductive adhesive is applied to the sockets (206) using an ink jet-type printer. Alternatively, if may be possible to combine steps 204 and 206 by injecting adhesive through the tool used to create the dimple in the substrate material.

Micro-components, which were separately formed in step 208 are placed in the sockets using an appropriate method as described in the afore-mentioned co-pending application Ser. No. 10/214,769. As previously described, the micro-components are typically coated with a phosphor material for visible light emission. In an exemplary embodiment of micro-component forming process step 208, the micro-components are coated with phosphor by immersing the micro-components in a bath containing a sluny of phosphor particles so that the particles adhere to the micro-component surface. The micro-components are then removed from the slurry and subjected to a curing process, e.g., a furnace, oven or other heat source, to remove any solvents that were used to form the slurry, leaving a solid phosphor coating on the micro-component surface.

In step 212, the adhesive material that holds the micro-component in place is cured by applying heat for a predetermined time (based upon the manufacturer's recommendations), or at room temperature for a longer time (again, based on the manufacturer's specifications), introducing pressurized gas or other known adhesive curing method, then, the dielectric film is applied in liquid form by coating the substrate with a liquid dielectric material (step 214). The liquid dielectric material may be a polyimide (e.g., Kapton®), or other polymeric materials.

Application of liquid dielectric uses known techniques of web coating using web coating systems such as those commercially available from Rolltronics (Menlo Park, Calif.), Sheldahl, Inc. (Northfield, Minn.), Frontier Industrial Technology, Inc. (Towanda, Pa.) and Applied Films Corp. (Longmont, Colo.), among others. An exemplary coating system comprises a web-handling machine mounted inside a large vacuum chamber. The machine unwinds a web from a payoff reel, wraps it over a drum, which may be temperature-controlled to assist in film formation, and winds it onto a take-up reel. Each reel is driven indirectly via chain drive and a DC motor, allowing better control of web speed while developing a higher tension than would be possible with a motor and gear reduction box. The signal from an optical encoder is delivered to a process controller for speed control of one motor, and a measurement of the length unwound. The other motor is operated in regenerative mode to develop holdback tension. An exemplary deposition process for a coating stack of films comprises positioning the drum over a first deposition device, e.g., sprayer or evaporator. A fixed length of web is unwound in the first pass to deposit the first film. Then the motor direction is reversed, and a second film is deposited in a second pass. Next the drum may be moved sideways to position it over a second deposition device, which may be, e.g., a sprayer, evaporator, or ink jet head. The web direction is reversed a third time and the third coating is deposited in a single pass. In each case, web speed is determined according to the desired coating thickness and deposition rate. An alternative configuration includes one or more accumulators disposed between the payoff and take-up reels which allows sections of the web to dwell in certain stations along the processing line, for example, for deposition or curing a film for an extended period of time, without requiring all other steps in the process to pause or interfering with the tension of the web.

The dielectric film may be applied as a thin film using chemical vapor deposition (CVD), plasma CVD, or other vapor deposition methods, sputtering, or may be applied as a liquid "paint" such as one of the roll coat methods used in the coating of magnetic recording media. See, e.g., U.S. Pat. No. 6,322,010, the disclosure of which is incorporated herein by reference in its entirety. In the preferred embodiment, a liquid process is used to create a film on the order of 100 microns with relatively tight tolerances across the film, e.g., ±1%. The viscosity of the dielectric material in its liquid form is selected to ensure complete wetting of the surfaces of the micro-components to the extent that the micro-components should be covered, and to ensure uniformity of the film thickness. The key parameter to be observed in formation of the dielectric film is the uniformity of the dielectric properties so that the surface flashover (voltage breakdown that occurs on or above the surface of an insulator) and bulk dielectric breakdown characteristics are tightly controlled to minimize the possibility of arcing or voltage breakdown across any dielectric discontinuities when voltage is applied to electrodes corresponding to a given micro-component. A typical good dielectric material has a breakdown voltage in the range of 500 to 5000 volts per mil (about 200 to 2000 kV/cm) in the bulk, with a preferred range of 1000 volts per mil (400 kV/cm) or higher. The surface flashover field strength should also be in the range of 1000 volts per mil (400 kV/cm). This will be achieved partially through material selection and principally with the application of a thin coating, such as a resin or epoxy, to the surfaces of the electrodes and micro-component. This coating inhibits electron flow over the surface between the electrodes thereby raising its flashover voltage. In addition, a good loss tangent for the dielectric material, typically in the range of 0.01 to 0.1, at 100 kHz to 1 MHz is preferred. An exemplary range for dielectric constant in this frequency range is 3.5 to 5.

Wetting can be enhanced by the inclusion of surfactants in the liquid dielectric material to manage the surface energy of the liquid. Alternatively, or in addition, surfactants may also be applied to the outer surface of the micro-components to facilitate complete wetting. Obtaining a uniform thickness of the dielectric film can be further facilitated by use of a scraper or knife edge which is precisely positioned over the drum to remove any excess thickness as the web material leaves the drum.

Viscosity and surface tension of the liquid dielectric may also be controlled to produce a positive, neutral, or negative meniscus around each micro-component. In one embodiment, a negative meniscus results in a surface depression abutting the micro-component The dielectric material is then cured (step 216) to form a uniform film at least partially covering the micro-components, embedding them in place within the combination of the first substrate and the dielectric layer formed using the liquid dielectric. Curing is typically achieved by passing the web material through a heated chamber set to a temperature appropriate for curing the dielectric film. As the liquid dielectric is typically a commercially-available product, the temperature and duration of the curing step will be based upon the manufacturer's recommendations for the selected liquid material. As will be apparent to those of skill in the art, some variation of the recommended curing conditions may be incorporated for compatibility with the particular web manufacturing equipment or process that is being used. The portion of web material to be cured may be paused or slowed by the use of an accumulator, or the heated chamber may have a length designed to provide a sufficient duration within the chamber while the web material moves at a predetermined speed, or a combination of the two.

In the preferred embodiment, a portion of the micro-component is left exposed after curing of the dielectric film. Considering the embodiment of FIG. 5 as an example, the first application of liquid dielectric resulted in a dielectric layer 65a that covers just under one-half the height of the micro-component 50.

Electrodes are formed by applying a conductive liquid to the upper surface of the second substrate (step 218). The electrodes may be patterned using known lithographic techniques, e.g., conductive film deposition over the entire area, photoresist deposition, masked exposure and development followed by etching, or by printing, e.g., ink-jet printing, or by using liquids that are selectively drawn to the desired locations using one or a combination of characteristics of the liquid including surface tension, viscosity, thickness and electrical conductivity. In the preferred embodiment, a conductive ink is applied using an ink-jet printing technique. The ink contains copper, indium oxide, silver, or other conductive material carried in an epoxy or epoxy-like material. Appropriate conductive inks are commercially available and will have electrical conductivity in the range of 1250 mhos/cm or higher. After printing, the conductive ink is cured based on the manufacturer's recommendations (step 220).

In an alternate embodiment, the characteristics of the liquid dielectric material from which the dielectric layer is formed can be selected to create a shallow trough or depression connecting the micro-components in a line, e.g., a negative meniscus is formed upon deposition or a small amount of shrinkage can occur during curing to create the depression. The conductive liquid used to form the electrodes is selected with a viscosity and thickness such that it will be drawn into the depressions to fill them, thus creating a conductive line running between the micro-components. It is important, however, that the conductive film not stick to the micro-components themselves. Therefore, the liquid conductor should include a component to prevent wetting of the micro-component surface. An additional step in this alternate embodiment can be to scrape away any excess conductor from the surface of the dielectric layer except where it has filled the depressions. For example, a squeegee or other scraper can be used to level the outer surface of the assembly so that the conductor is flush with the outer surface of the dielectric layer. After deposition of the conductive film, an appropriate curing step is performed, generally according to specifications provided by the material manufacturer.

If an unpatterned conductive film has been deposited, i.e., a solid layer of conductive film is produced, the film can be patterned using conventional photolithographic methods in which a photoresist layer is formed on top of the conductive film, the photoresist is exposed through a mask bearing the desired electrode pattern, the photoresist is developed so that the desired electrode pattern remains, the conductor is selectively etched away using chemical or plasma etching, and the remaining photoresist is then stripped, leaving behind the patterned electrodes. Other forms of patterning are known to those of skill in the art, including e-beam writing or laser ablation.

In an alternate method for formation of electrodes using photolithographic methods, after formation of a conductive layer, a coating of photosensitive material, e.g., photoresist, is deposited on top of the conductive layer. A contact mask is provided which is formed from a flexible optical waveguide having a wide surface area which covers all or a significant area of a section of the web material. An exemplary waveguide device is described in U.S. Pat. No. 6,091,874, which is incorporated herein by reference in its entirety. The waveguide material is patterned so that the index of refraction of its cladding is selectively increased so that it "leaks" at positions corresponding to the desired locations of the electrodes to be defined. Light, typically from a laser light source or a high intensity lamp, of an appropriate wavelength for exposure of the photoresist is coupled into the waveguide using conventional coupling means. The flexible waveguide is aligned with the underlying pattern over the area of photoresist-coated conductive layer on which the pattern is to be formed. The photoresist is then exposed by the light emitted from the selective leaks in the waveguide. After the photoresist is cured and the unexposed resist is removed, the conductive material is selectively etched to form the electrodes at the desired locations.

In embodiments of the device in which multiple layers of conductors are required, see, e.g., the embodiments of FIGS. 5–7, after curing and, if required, patterning, the conductive film to form the electrodes, another deposition of liquid dielectric is performed as described above by passing the web material through the liquid dielectric deposition process. After formation of a second dielectric layer, another step is performed to create additional electrodes. Referring to FIG. 7 to illustrate, dielectric layers 65*a*, 65*b* and 65*c* alternate with second address electrode 85, first address electrode 80 and first sustain electrode 70, respectively, such that the web manufacturing process includes three separate steps for depositing liquid dielectric to form the dielectric layers and three separate steps for depositing a conductive liquid to form the electrodes.

After formation of the final (uppermost) electrodes, a protective layer, e.g., layer 20 in FIG. 7, is applied, either using a liquid dielectric uniformly coated over the assembly, or a flexible sheet material laminated over the top of the light-emitting panel assembly. If a liquid is used, the assembly must again be processed through the appropriate curing step (224). Then, the panels are cut to the desired size in the dicing step (226).

In one embodiment, prior to applying the top layer in step 222, an optional contrast enhancement layer may be included in which the micro-components are surrounded by a dark, preferably black, background field. One method for applying this black mask layer includes coating the area surrounding the micro-components, i.e., the dielectric layer and conductive lines, with a slurry of carbon black particles (step 219) or a similar black curable liquid. The coating can be applied by uniform application of the slurry to the upper surface of the assembly, then using a squeegee to remove the material from the micro-components. Alternatively, the slurry can be applied using an ink jet-type printer, with the printer target being aligned to selectively apply the slurry to create a ring or other pattern surrounding each micro-component. After deposition of the coating, a curing step is performed to dry the black mask layer by removing solvents used to make the slurry. In yet another alternative method for formation of the black mask layer, after curing of the carbon black slurry, a photolithographic process can be used to selectively etch the black film from the surface of the micro-components.

In another alternate embodiment of the web manufacturing process, a hybrid sheet/liquid process is used. As described with regard to the first embodiment of the web manufacturing process shown in FIG. 9, a second substrate is applied as a sheet material, where openings are formed in the second substrate to correspond to the locations of the micro-components. However, in this embodiment, the openings are not as tightly toleranced to fit the micro-components, but are larger, thus requiring less precision in the alignment of the openings to the micro-components. Then, a liquid dielectric with dielectric characteristics close to or matching those of the second substrate material is applied by an ink-jet process, or may be coated over the entire surface. If coated over the entire surface, the use of a scraper or squeegee will assist in forcing the liquid into the spaces between the micro-components and the inside edges of the second substrate openings. The viscosity and surface energy of the liquid dielectric material are selected to wet the surfaces of the micro-components and file any gaps between the second substrate and the micro-components. After curing, a continuous dielectric film surrounds the micro-components as in the previous-described embodiments.

In yet another embodiment, after formation of the protective layer (step 224) and before dicing, an RF screen is formed by depositing a conductive liquid over the entire top surface of the assembly, where the conductive liquid is clear or becomes clear when cured. For example, indium-tin-oxide (ITO) can be used, however, other transparent conductive coatings are known, including transparent gold (TPG) and transparent silver or aluminum-based coatings. It may be desirable to coat an additional protective dielectric layer over RF screen, which may be performed using a liquid dielectric material followed by curing, or by applying a sheet of dielectric materials over the assembly. In addition to use as a RF screen, transparent conductive materials can be used in the construction of the light-emitting displays so as to facilitate implementation as a heads-up display for use in motor vehicles for purposes of facilitating a driver's ability to read displays without diverting his or her eyes away from the road.

Other embodiments and uses of the present invention will be apparent to those skilled in the art from consideration of this application and practice of the invention disclosed herein. The present description and examples should be considered exemplary only, with the true scope and spirit of the invention being indicated by the following claims. As will be understood by those of ordinary skill in the art, variations and modifications of each of the disclosed embodiments, including combinations thereof, can be made within the scope of this invention as defined by the following claims.

What is claimed is:

1. A method comprising:
   providing a first substrate, the first substrate having a first conductor formed thereon;
   disposing at least one micro-component adapted to emit radiation at a first location on the first substrate corresponding to the first conductor;
   forming a dielectric layer on the first substrate;
   forming a second conductor on the dielectric layer to interact with the first conductor to excite the micro-component; and
   applying a top layer over the dielectric layer and the second conductor.

2. The method of claim 1, wherein the step of forming a dielectric layer on the first substrate comprises:
   depositing a liquid dielectric material onto the first substrate to electrically isolate the micro-component from any other micro-component on the first substrate; and
   curing the liquid dielectric material to form a dielectric layer.

3. The method of claim 1, wherein the step of forming the second conductor comprises:
   depositing a conductive liquid on top of the dielectric layer at a second location adapted to interact with the first conductor to excite the micro-component; and
   curing the conductive liquid to create a conductive layer for providing the second conductor.

4. The method of claim 1, further comprising:
   coating the micro-component with a phosphor material.

5. The method of claim 1, further comprising:
   immersing the micro-component in a slurry of phosphor particles to form a phosphor coating; and
   curing the phosphor coating formed on the micro-component.

6. The method of claim 3, further comprising:
   depositing a liquid black mask layer onto the first substrate and the conductive layer; and
   curing the liquid mask material to form a black mask layer.

7. The method of claim 3, further comprising:
   photolithographically patterning the conductive layer to form the second conductor.

8. The method of claim 7, wherein the step of photolithographically patterning comprises:
   selectively exposing a photosensitive material by contacting the photosensitive material with a leaky optical waveguide.

9. The method of claim 1, wherein the first substrate has a dimple formed therein at the first location.

10. The method of claim 9, wherein an adhesive material is applied within the dimple for securing the micro-component in the dimple.

11. The method of claim 3, wherein the step of depositing a conductive liquid comprises printing an electrode pattern with a conductive ink.

12. The method of claim 11, wherein the printing comprises inkjet printing.

13. The method of claim 2, wherein the liquid dielectric material has a surface tension adapted to provide a uniform thickness across the first substrate.

14. The method of claim 2, wherein the liquid dielectric material includes a surfactant.

15. The method of claim 1, further comprising disposing an RF screen over the top layer.

16. A method comprising:
   providing a first dielectric substrate material;
   printing an electrode on the first dielectric material;
   forming a socket at a location in the first dielectric material;
   disposing a micro-component adapted to emit light in the socket;
   forming a dielectric layer on the first dielectric material;
   printing a second electrode over the dielectric layer; and
   applying a top layer over the dielectric layer, the second electrode, and the micro-component.

17. The method of claim 16, wherein the step of providing the first dielectric substrate material comprises:
   feeding the first dielectric substrate material from a payout reel in a web coating machine.

18. The method of claim 16, wherein the step of forming a dielectric layer on the first dielectric material comprises:
   applying a liquid dielectric material over the first dielectric material, the first plurality of electrodes, and at least a portion of the micro-component; and
   curing the liquid dielectric material to form the dielectric layer.

19. The method of claim 16, wherein the step of printing the second electrode over the dielectric layer comprises:
   printing the second electrode over the dielectric layer using a conductive ink; and
   curing the conductive ink.

20. The method of claim 16, further comprising:
   applying an adhesive material within the socket for securing the micro-component.

21. The method of claim 16, wherein the step of disposing the micro-component in the socket comprises using electrostatic sheet transfer to place the micro-component into the socket.

22. The method of claim 16, wherein the step of printing the second electrode over the dielectric layer comprises inkjet printing.

23. The method of claim 18, wherein the liquid dielectric material has a surface tension adapted to provide a uniform thickness across the first substrate.

24. The method of claim 18, wherein the liquid dielectric material includes a surfactant.

25. The method of claim 16, further comprising: disposing an RF screen over the top layer.

26. The method of claim 16, further comprising: coating the micro-component with a phosphor material.

27. The method of claim 16, further comprising:
   immersing the micro-component in a slurry of phosphor particles to form a phosphor coating; and
   curing the phosphor coating formed on the micro-component.

28. The method of claim 19, further comprising:
   depositing a liquid black mask layer onto the first substrate and the conductive ink; and
   curing the liquid mask material to form a black mask layer.

29. A method for forming a flexible light emitting panel comprising:
   feeding a first dielectric substrate material from a payout reel in a web coating machine;
   printing a first electrode on the first dielectric material;
   forming a socket at a location in the first dielectric material;
   disposing a micro-component adapted to emit light in the socket;
   aligning a second sheet material having dielectric properties over the first dielectric substrate material and the first electrode, wherein the second dielectric sheet material has an opening therethrough corresponding to the location, the opening having a diameter larger than an outer diameter of the micro-component; so that a gap is created between an inner diameter of each opening and the outer diameter of each micro-component;

providing a dielectric material over at least a portion of the second sheet material so that the gap corresponding to the micro-component is filled;

printing a second electrode over the second sheet material; and applying a top layer over the second sheet material, the second electrode and the micro-component.

30. The method of claim 29, wherein the step of provide the dielectric material comprises:

applying a liquid dielectric material over at least a portion of the second sheet material so that the gap corresponding to the micro-component is filled, the liquid dielectric material having dielectric properties adapted for control of electric field and breakdown characteristics of the micro-component; and curing the liquid dielectric material.

31. The method of claim 29, wherein the step of printing the second electrode comprises:

printing the second electrode over the second sheet material using a conductive ink; and curing the conductive ink.

32. The method of claim 29, further comprising:

applying an adhesive material within the socket for securing the micro-component in the socket.

33. The method of claim 29, wherein the step of disposing the micro-component in the socket comprises:

using electrostatic sheet transfer to place the micro-component into the socket.

34. The method of claim 29, wherein the step of printing the second electrode comprises inkjet printing.

35. The method of claim 30, wherein the liquid dielectric material includes a surfactant.

36. The method of claim 29, further comprising disposing an RF screen over the top layer.

37. The method of claim 29, further comprising: coating the micro-component with a phosphor material.

38. The method of claim 29, further comprising:

immersing the micro-component in a slurry of phosphor particles to form a phosphor coating; and curing the phosphor coating formed on the micro-component.

39. The method of claim 29, further comprising:

depositing a liquid black mask layer onto the first substrate and the conductive ink; and curing the liquid mask material to form a black mask layer.

* * * * *